US012643838B2

(12) United States Patent　　　　(10) Patent No.:　US 12,643,838 B2
Goto et al.　　　　　　　　　　　(45) Date of Patent:　　　Jun. 2, 2026

(54) METHOD FOR PRODUCING METAL CARBIDE, METHOD FOR PRODUCING HYDROCARBON, AND METAL CARBIDE COMPOSITION

(71) Applicants: THE DOSHISHA, Kyoto (JP); DAIKIN INDUSTRIES, LTD., Osaka (JP)

(72) Inventors: Takuya Goto, Kyotanabe (JP); Takashi Watanabe, Kyotanabe (JP); Yuta Suzuki, Kyotanabe (JP); Haruka Fukuda, Kyotanabe (JP); Atsuya Yamada, Kyotanabe (JP); Tomohiro Isogai, Osaka (JP); Yosuke Kishikawa, Osaka (JP); Akiyoshi Yamauchi, Osaka (JP)

(73) Assignees: THE DOSHISHA, Kyoto (JP); DAIKIN INDUSTRIES, LTD., Osaka (JP)

(*) Notice: Subject to any disclaimer, the term of this patent is extended or adjusted under 35 U.S.C. 154(b) by 258 days.

(21) Appl. No.: 18/619,620

(22) Filed: Mar. 28, 2024

(65) Prior Publication Data

US 2024/0286974 A1　　Aug. 29, 2024

Related U.S. Application Data

(63) Continuation of application No. PCT/JP2022/037022, filed on Oct. 3, 2022.

(30) Foreign Application Priority Data

Oct. 4, 2021　(JP) ................................. 2021-163668

(51) Int. Cl.
*C07C 1/12*　　　　(2006.01)
*C01B 32/935*　　　(2017.01)
(Continued)

(52) U.S. Cl.
CPC .............. *C07C 1/12* (2013.01); *C01B 32/935* (2017.08); *C01B 32/942* (2017.08); *C01D 15/02* (2013.01); *C01F 11/02* (2013.01); *C01P 2002/72* (2013.01)

(58) Field of Classification Search
CPC ....... C07C 1/12; C01B 32/935; C01B 32/942; C01D 15/02; C01F 11/02; C01P 2002/72
See application file for complete search history.

(56) References Cited

U.S. PATENT DOCUMENTS 4,009,219 A　2/1977　Tamers
4,137,295 A　1/1979　Tamers

FOREIGN PATENT DOCUMENTS

CN　　112391643 A　2/2021
EP　　4 394 086 A1　7/2024
(Continued)

OTHER PUBLICATIONS

International Preliminary Report on Patentability issued Apr. 9, 2024 in Application No. PCT/JP2022/037022.
(Continued)

*Primary Examiner* — Ellen M McAvoy
(74) *Attorney, Agent, or Firm* — Sughrue Mion, PLLC

(57) ABSTRACT

A method for producing a hydrocarbon, including: preparing a molten salt containing an oxide of a first metal; adding carbon dioxide to the molten salt; obtaining precipitates containing a first metal carbide by applying a voltage to the molten salt containing carbon dioxide; and obtaining a gas containing a hydrocarbon and a hydroxide of the first metal by hydrolyzing the first metal carbide.

4 Claims, 20 Drawing Sheets

(51) Int. Cl.
　　 *C01B 32/942*　　(2017.01)
　　 *C01D 15/02*　　(2006.01)
　　 *C01F 11/02*　　(2006.01)

(56) References Cited

FOREIGN PATENT DOCUMENTS

| | | | |
|---|---|---|---|
| JP | 61-178412 | A | 8/1986 |
| JP | 63-112409 | A | 5/1988 |
| JP | H02-256626 | A | 10/1990 |
| JP | 2018-035328 | A | 3/2018 |

OTHER PUBLICATIONS

Extended European Search Report dated Mar. 28, 2025 in Application No. 22878488.0.

JM McEnaney, et al., "A cyclic electrochemical strategy to produce acetylene from CO2, CH4, or alternative carbon sources." Sustain Energy Fuels, 4:2752-2759, 2020, 14 total pages, vol. 4, No. 6.

Xinxin Liang et al., "Electrochemical Reduction of Carbon Dioxide and Iron Oxide in Molten Salts to Fe/Fe3C Modified Carbon for Electrocatalytic Oxygen Evolution," Angewandte Chem., Jan. 18, 2021, pp. 2148-2152, 5 total pages vol. 133, No. 4.

D.C. Topor et al., "Molybdenum Carbide Coatings Electrodeposited from Molten Fluoride Bath," Journal of the Electrochemical Society, Feb. 1988, pp. 384-387, 6 total pages vol. 135, No. 2.

Hideki Yabe et al., "The Effect of Silver Ion on Electrodeposition of Tungsten Carbide From Molten Chloride," Electrochimica Acta, Jan. 1990, pp. 187-189, 3 total pages, vol. 35, No. 1.

International Search Report for International Application No. PCT/JP2022/037022 dated Dec. 20, 2022.

METHOD FOR PRODUCING METAL CARBIDE, METHOD FOR PRODUCING HYDROCARBON, AND METAL CARBIDE COMPOSITION

CROSS REFERENCE TO RELATED APPLICATIONS

This application is a Rule 53(b) Continuation of International Application No. PCT/JP2022/037022 filed Oct. 3, 2022, claiming priority based on Japanese Patent Application No. 2021-163668 filed Oct. 4, 2021, the disclosures of which are incorporated herein by reference in their respective entireties.

TECHNICAL FIELD

The present invention relates to a method for producing a metal carbide, a method for producing a hydrocarbon, and a metal carbide composition.

BACKGROUND ART

Acetylene is an industrially important substance as a raw material for various organic compounds. Acetylene is usually obtained by the reaction of a metal carbide (mainly calcium carbide) and water.

Calcium carbide is generally obtained by heating a mixture of quicklime (calcium oxide) and coke to a high temperature in an electric furnace (for example, Patent Document 1). Patent Document 2 proposes that the coke is briquetted in advance and mixed with quicklime. According to Patent Document 2, calcium carbide can be obtained thereby more effectively. Patent Document 3 proposes a method for producing lithium carbide by reacting metallic lithium obtained by melting and electrolyzing lithium chloride with carbon powder such as carbon black. Non Patent Document 1 proposes a method for producing lithium carbide by reacting metallic lithium obtained by molten salt electrolysis of lithium hydroxide with a carbon source such as carbon dioxide and recycling the lithium hydroxide produced as a by-product in molten salt electrolysis.

PRIOR ART DOCUMENTS

Patent Documents

Patent Document 1: JP 61-178412 A
Patent Document 2: JP 2018-35328 A
Patent Document 3: JP 2-256626 A

Non Patent Document

Non Patent Document 1: McEnaney J M, Rohr B A, Nielander A C, Singh A R, King L A, Norskov J K, Jaramillo T F "A cyclic electrochemical strategy to produce acetylene from $CO_2$, $CH_4$, or alternative carbon sources." Sustain Energy Fuels 4:2752-2759 (2020)

SUMMARY

The present disclosure includes the following embodiments.

A method for producing a metal carbide, comprising: preparing a molten salt containing an oxide of a first metal; adding carbon dioxide to the molten salt; and obtaining precipitates containing a first metal carbide by applying a voltage to the molten salt containing carbon dioxide.

Effects

The present disclosure provides a method for producing a metal carbide using carbon dioxide as a carbon source and metal oxide as a metal source, a method for producing a hydrocarbon from the metal carbide obtained using carbon dioxide as a carbon source and metal oxide as a metal source, and a metal carbide composition.

DESCRIPTION OF EMBODIMENTS

In the method for producing a metal carbide of the present disclosure, a voltage is applied to a molten salt containing a metal oxide and carbon dioxide ($CO_2$) to obtain a metal carbide. This method using molten salts allows the reaction to proceed rapidly and efficiently at relatively low temperatures below 800° C. to obtain metal carbide. In addition, since the metal oxide is used, the solubility of carbon dioxide into the molten salt is increased. The target metal carbide can therefore be obtained with higher productivity, selectivity, and safety in a smaller electrolytic bath. $CO_2$, which is said to be a cause of global warming, can also be effectively utilized as a carbon source.

The present disclosure includes hydrolyzing the metal carbide by the aforementioned method, to obtain a hydrocarbon. This method can efficiently obtain high-purity hydrocarbons. A hydrocarbon (typically, acetylene), which is industrially important, can also be produced from $CO_2$, and the method of the present disclosure is very useful from the perspective of environmental conservation.

The present disclosure includes reusing the metal hydroxide produced as a by-product when producing the hydrocarbon as a metal source for producing the aforementioned metal carbide. This creates a recycling system that includes the production of first metal carbide using oxides of the first metal and the production of hydrocarbons using the first metal carbide. Resources can be used effectively.

The present disclosure includes a carbide composition containing a carbide of the first metal. This carbide composition can be utilized for producing a hydrocarbon.

[Method for Producing Metal Carbide]

Figure 1:
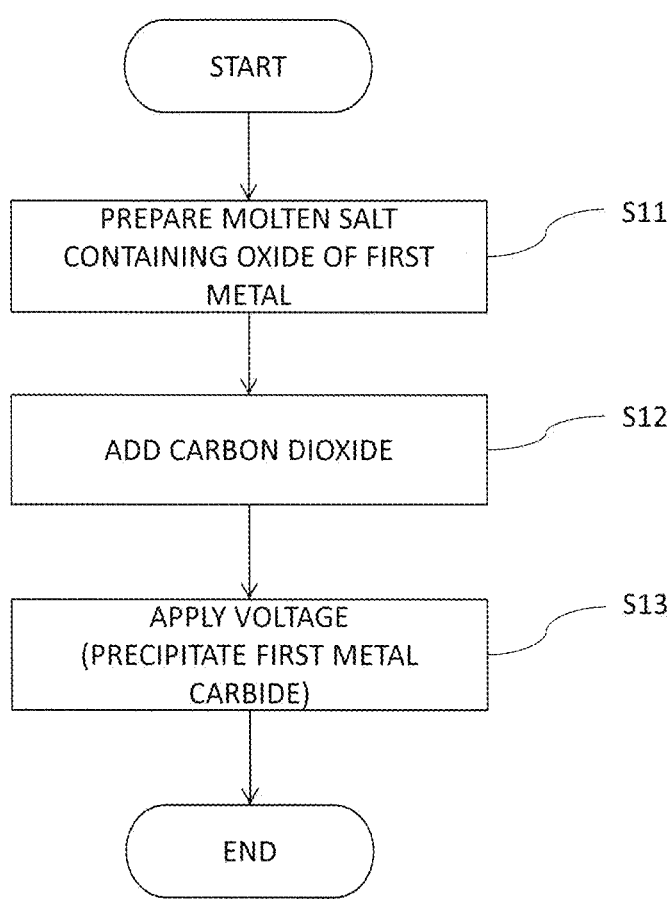
FIG. 1 is a flowchart showing a method for producing a metal carbide according to the present disclosure.

The method for producing a metal carbide according to the present disclosure comprises: preparing a molten salt containing an oxide of a first metal; adding carbon dioxide to the molten salt; and applying a voltage to the molten salt containing carbon dioxide, to obtain precipitates containing a carbide of the first metal. FIG. 1 is a flowchart showing the method for producing a metal carbide according to the present disclosure.

(I) Preparation of Molten Salt (S11)

First, a molten salt containing an oxide of a first metal is prepared. The oxide of the first metal is the metal source of the target metal carbide. For convenience of description, a metal salt (including a metal oxide) contained in the electrolytic bath will be referred to as a molten salt, even if it is not completely ionized.

(Oxide of First Metal)

The oxide of the first metal is not limited and is appropriately selected depending on the target metal carbide. The first metal is preferably at least one selected from the group consisting of alkali metals and alkaline earth metals. Alkali metals and alkaline earth metals have lower ionization energy than other metals and are more easily ionized.

Examples of the alkali metals include at least one selected from the group consisting of lithium (Li), sodium (Na), potassium (K), rubidium (Rb), cesium (Cs), and francium (Fr). Preferable examples of the alkali metals include at least one selected from the group consisting of Li, Na, K, Rb, and Cs. At least one selected from the group consisting of Li, Na, K, and Cs is more preferable.

Examples of the alkaline earth metals include at least one selected from the group consisting of beryllium (Be), magnesium (Mg), calcium (Ca), strontium (Sr), barium (Ba), and radium (Ra). Preferable examples of the alkaline earth metals include at least one selected from the group consisting of Mg, Ca, Sr, and Ba.

In consideration of the reactivity of the oxide of the first metal with water, Li, Na, K, and Ca are preferable as the first metal. Na and Ca are more preferable in terms of low cost, and Li and Ca are more preferable in terms of handleability such as safety and toxicity.

Li, Na, K, and Cs are preferable as the first metal for high solubility of the hydroxide in water. The high solubility of the hydroxide of the first metal in water enhances the recycling efficiency of the first metal in the subsequent step. In the method for producing a hydrocarbon, the metal carbide is hydrolyzed and the hydroxide of the first metal is produced as a by-product together with the hydrocarbon. Hydrocarbons are generally difficult to dissolve in water, and they can be easily extracted as a gas. Carbon contained in the precipitates is settled or suspended in water. When the hydroxide of the first metal as a by-product is dissolved in water, carbon can be removed by filtration efficiently. The hydroxide of the first metal can be recovered by removing water from the filtrate. The oxide of the first metal is obtained by dehydrating the hydroxide of the first metal. The higher the solubility of the hydroxide of the first metal in water, the easier the oxide of the first metal can be recovered. The oxide of the first metal obtained is reused for preparing the aforementioned molten salt. Meanwhile, the lower the solubility of the hydroxide of the first metal in water, the lower the energy required for its recover. For reducing the energy, the first metal is preferably Ca.

The amount of the oxide of the first metal contained in the molten salt is not limited. In view of the reaction efficiency, the number of moles of the oxide of the first metal is preferably 1 mol % or more, more preferably 2 mol % or more, particularly preferably 3 mol % or more, relative to the total number of moles of the molten salt in the electrolytic bath. The number of moles of the oxide of the first metal is preferably 20 mol % or less, more preferably 15 mol % or less, particularly preferably 10 mol % or less, relative to the total number of moles of the molten salt in the electrolytic bath. In one embodiment, the number of moles of the oxide of the first metal is 1 mol % or more and 20 mol % or less, relative to the total number of moles of the molten salt in the electrolytic bath.

(Other Metal Salt)

The molten salt preferably contains a metal salt other than the oxide of the first metal. The other metal salt mainly function as an electrolyte in the electrolytic bath. Also, the other metal salt facilitates melting of the oxide of the first metal. Examples of the other metal salt include a salt of ions of a metal (hereinafter referred to as second metal) and their counter ions (hereinafter referred to as second anions).

The second metal and the first metal may be the same or different. When the second metal is the same as the first metal, the carbide of the first metal is easily generated. When the second metal is the same as the first metal, the second anion is other than oxide ions.

The other metal salt is not limited, as long as the metal carbide that is a target substance can be stably precipitated. The other metal salt is preferably melted at a temperature of 800° C. or less.

Examples of the second metal include alkali metals, alkaline earth metals, rare earth elements, aluminum (Al), gallium (Ga), indium (In), thallium (Tl), zinc (Zn), cadmium (Cd), gold (Au), silver (Ag), and copper (Cu). The alkali metal and the alkaline earth metal are as described above. Examples of the rare earth element include scandium (Sc), yttrium (Y), the lanthanoid element, and the actinoid element. At least one selected from the group consisting of alkali metals and alkaline earth metals is preferable since the melting temperature of the other metal salt tends to be low.

Examples of the second anion include carbonate ions ($CO_3^{2-}$), sulfate ions, phosphate ions, nitrate ions, acetate ions, carboxylate ions, oxide ions ($O_2^-$), and halogen ions. Halogen ions are preferable since the melting temperature of the other metal salts tends to be low. Halogens have a large electron affinity.

Examples of the halogens include at least one selected from the group consisting of fluorine (F), chlorine (Cl), bromine (Br), iodine (I), and astatine (At). Preferable examples of the halogens include at least one selected from the group consisting of F, Cl, Br, and I. F and/or Cl is preferable. F is preferable since the solubility of the oxide of the first metal and/or $CO_2$ can be improved.

The second anion preferably contains an oxide ion since $CO_2$ is easily ionized. Examples of the oxide of the second metal include an oxide of at least one metal selected from the group consisting of alkali metals and alkaline earth metals different from the first metal.

Specific examples of the other metal salts include alkali metal halides such as LiF, NaF, KF, RbF, CsF, LiCl, NaCl, KCl, RbCl, CsCl, LiBr, NaBr, KBr, RbBr, CsBr, LiI, NaI, KI, RbI, and CsI; alkaline earth metal halides such as $MgF_2$, $CaF_2$, $SrF_2$, $BaF_2$, $MgCl_2$, $CaCl_2$, $SrCl_2$, $BaCl_2$, $MgBr_2$, $CaBr_2$, $SrBr_2$, $BaBr_2$, $MgI_2$, $CaI_2$, $SrI_2$, and $BaI_2$; rare earth element halides such as $AlCl_3$; oxides of metals other than the first metal such as $Li_2O$ and CaO; metal carbonates such as $Li_2CO_3$, $Na_2CO_3$, and $K_2CO_3$; and metal nitrates such as $LiNO_3$, $NaNO_3$, and $KNO_3$. At least one selected from the group consisting of lithium salt, sodium salt, and potassium salt is preferable. Chlorides and/or fluorides of at least one selected from the group consisting of Li, Na, and K are more preferable.

One of the other metal salts may be used alone, or two or more of them may be used in combination. It is preferable to use two or more other metal salts in combination since the melting temperature is easily reduced. Examples include combinations of a plurality of chlorides, combinations of a plurality of fluorides, and combinations of one or more chlorides and one or more fluorides. Specific examples include a combination of LiCl and KCl, a combination of LiCl, KCl, and $CaCl_2$, a combination of LiF, NaF, and KF, a combination of NaF and NaCl, and a combination of NaCl, KCl, and $AlCl_3$.

In the combination of a plurality of metal salts, the compounding ratio of the metal salts is not limited. For example, in the combination of LiCl and KCl, the number of moles of LiCl may be 30 mol % or more, 45 mol % or more, or 50 mol % or more, relative to the total number of moles of LiCl and KCl. The number of moles of LiCl may be 90 mol % or less, 70 mol % or less, or 65 mol % or less, relative to the total number of moles of LiCl and KCl. In one embodiment, the number of moles of LiCl is 45 mol % or more and 90 mol % or less, relative to the total number of moles of LiCl and KCl.

(II) Addition of Carbon Dioxide (S12)

Next, a gas containing carbon dioxide is added to the molten salt in a molten state. The gas containing carbon dioxide (hereinafter sometimes referred to as $CO_2$ gas) in a gaseous state is brought into contact with the molten salt in a liquid state. The $CO_2$ gas may be blown into the gas phase of the electrolytic bath and brought into contact with the liquid surface of the molten salt, or the $CO_2$ gas may be blown into the molten salt. The $CO_2$ gas may be a mixed gas of $CO_2$ and an inert gas (typically, argon). A sufficient amount of the $CO_2$ gas may be added to the molten salt before applying a voltage, or the $CO_2$ gas may be added to the molten salt while applying a voltage.

$CO_2$ blown in can be not only physically dissolved in the molten salt but also ionized and dissolved in the electrolytic bath as carbonate ions ($CO_3^{2-}$). In the molten salt, the first metal ions and oxide ions ($O^{2-}$) are generated due to the dissociation of the oxide of the first metal. $CO_2$, for example, can react with the aforementioned oxide ions present in the molten salt to form carbonate ions ($CO_3^{2-}$). That is, the oxide of the first metal increases the amount of $CO_2$ dissolved in the molten salt, to improve the productivity.

When the first metal is Li, lithium ions ($Li^+$) and oxide ions ($O^{2-}$) are generated in the molten salt, due to the dissociation of the oxide of the first metal (Formula 1). For example, $CO_2$ reacts with the aforementioned oxide ions, to form carbonate ions ($CO_3^{2-}$) (Formula 2).

$$Li_2O \rightarrow 2Li^+ + O^{2-} \tag{Formula 1}$$

$$CO_2 + O^{2-} \rightarrow CO_3^{2-} \tag{Formula 2}$$

The amount of $CO_2$ gas to be blown in may be appropriately set depending on the amount of the oxide of the first metal. The amount of $CO_2$ gas to be blown in is, for example, the equivalent amount or more of the oxide of the first metal contained in the molten salt, in consideration of the absorption efficiency of the gas into the molten salt. When 29.9 g of lithium oxide is contained in the molten salt as the oxide of the first metal, the amount of $CO_2$ gas to be blown in may be 44.0 g or more, or may be 440 g or more. The use of an appropriate amount of $CO_2$ gas reduces energy loss, temperature drop of molten salts, decomposition reactions, etc., and also improves the yield of the target carbide.

The bubble size of the $CO_2$ gas to be blown in is desirably smaller, for promoting the dissolution of $CO_2$ into the molten salt. The bubble size of the $CO_2$ gas is preferably 10 mm or less, more preferably 1 mm or less. The bubble size of the $CO_2$ gas may be 100 nm or more, or may be 1 μm or more. The bubble size of the $CO_2$ gas can be made finer, for example, by bubbling through a porous material made of quartz glass or high-purity alumina, stirring with a stirrer, applying vibration, irradiation with ultrasonic waves.

The $CO_2$ gas is preferably preheated to a temperature close to that of the molten salt. Preheating can prevent the temperature drop and solidification of the molten salt.

(III) Application of Voltage (S13)

Subsequently, a voltage is applied to the molten salt. This results in the reduction of $CO_3^{2-}$ on the cathode, and precipitates containing the carbide of the first metal (first metal carbide) are obtained. Precipitates containing the first metal carbide are precipitated on the surface of an electrode (cathode) having a low potential. Carbon may be generated on the cathode as a by-product. Oxygen and a halogen gas such as chlorine may be generated on the anode.

When the first metal is Li, lithium carbide ($Li_2C_2$) is precipitated on the cathode as the first metal (Formula 3). On the cathode, carbon and metallic lithium can be generated due to side reactions (Formulas 4 and 5). Part or all of the carbon and metallic lithium generated in such side reactions can further react to form lithium carbide (Formula 6). Alternatively, metallic lithium can react with carbon dioxide physically dissolved in the molten salt to form lithium carbide (Formula 7).

$$2Li^+ + 2CO_3^{2-} + 10e^- \rightarrow Li_2C_2 + 6O^{2-} \tag{Formula 3}$$

$$2CO_3^{2-} + 8e^- \rightarrow 2C + 6O^{2-} \tag{Formula 4}$$

$$2Li^+ + 2e^- \rightarrow 2Li \tag{Formula 5}$$

-continued $$2Li + 2C \rightarrow Li_2C_2 \qquad \text{(Formula 6)}$$

$$2Li + 2CO_2 \rightarrow Li_2C_2 + 2O_2 \qquad \text{(Formula 7)}$$

Depending on the type of the metal and the conditions, the oxide of the first metal may further react with carbon dioxide, to generate the carbide of the first metal. For example, when the first metal is Li, lithium carbide can be generated (Formula 8).

$$Li_2O + 2CO_2 \rightarrow Li_2C_2 + 5/2O_2 \qquad \text{(Formula 8)}$$

$O_2^-$ is oxidized on the anode to generate oxygen (Formula 9).

$$2O^{2-} \rightarrow O_2 + 4e^- \qquad \text{(Formula 9)}$$

When the first metal is Na, K, or Ca, sodium carbide ($Na_2C_2$), potassium carbide ($K_2C_2$), or calcium carbide ($CaC_2$) is precipitated by a similar reaction. The same applies to another first metal.

$O_2^-$ is oxidized on the anode to generate oxygen. The oxygen generated on the anode is exhausted into the gas phase. The oxygen gas can be recovered and used for other applications.

The voltage is applied at a temperature at which the molten salt can be maintained in a molten state. The temperature of the electrolytic bath may be, for example, 350° C. or more, or may be 400° C. or more. The temperature of the electrolytic bath may be, for example, 800° C. or less, or may be 700° C. or less. In the present disclosure, the reaction proceeds at such relatively low temperatures, and thus the energy efficiency is high.

The applied voltage is set so that the cathode potential is between the potential at which carbon is precipitated (Ec) and the potential at which the first metal is precipitated (Em). This can improve the selectivity of the first metal carbide. When the potential of the cathode is excessively high (noble), carbon is mainly precipitated, and the amount of the target first metal carbide generated tends to decrease. When the potential of the cathode is excessively low (base), although the first metal carbide is generated, the metal with the noblest redox potential in the molten salt among the metals contained in the molten salt is mainly precipitated. When a plurality of metals having similar redox potentials in the molten salt are present in the molten salt, alloys of a plurality of metals may be precipitated. For example, when the molten salt contains LiCl, KCl, and $Li_2O$ (5 mol %), the cathode potential may be 0.0 V or more and 1.0 V or less ($Li^+$/Li standard). The voltage may be direct current, intermittent (pulse electrolysis), or superimposed alternating current. The potentials Ec and Em can be determined in the molten salt used, for example, by performing cyclic voltammetry using Ni electrodes.

The current value may be appropriately set according to the amount of $CO_2$ supplied per unit time. The current value is set, for example, so that $CO_3^{2-}$ to be generated by the reaction of $CO_2$ and $CO_2$ with $O_2^-$ in the molten salt is larger than the $CO_2$ and $CO_3^{2-}$ consumed at the cathode per unit time, so as not to decrease the concentration of $CO_2$ and $CO_3^{2-}$ in the molten salt.

The material of the cathode is not limited. Examples of the material of the cathode include metals such as Ag, Cu, Ni, Pb, Hg, Tl, Bi, In, Sn, Cd, Au, Zn, Pd, Ga, Ge, Fe, Pt, Ru, Ti, Cr, Mo, W, V, Nb, Ta, Zr, and their alloys, and carbon materials such as glassy carbon, natural graphite, isotropic graphite, pyrolytic graphite, plastic formed carbon, and electrically conductive diamond.

The material of the anode is not limited. Examples of the material of the anode include Pt, electrically conductive metal oxide, glassy carbon, natural graphite, isotropic graphite, pyrolytic graphite, plastic formed carbon, and boron-doped diamond. Examples of the electrode made of electrically conductive metal oxide include a transparent electrically conductive electrode formed into a film using a mixed oxide of indium and tin on glass, which is called ITO electrode, an electrode formed into a film of the oxide of a platinum group-metal such as ruthenium and iridium on a substrate such as titanium, which is called DSA electrode (trademark of De Nora Permelec Ltd.), and $La_{1-x}Sr_xFeO_{3-\delta}$ sintered electrode, which is recently developed at Doshisha University. Oxide-based anodes are preferable. Oxide-based anodes are less likely to be consumed by oxidation reactions. (Metal Carbide)

The metal carbide to be obtained is mainly a carbide of the first metal (first metal carbide). In consideration of the hydrolyzability in the subsequent step, the first metal carbide is preferably at least one selected from the group consisting of $Li_2C_2$, $Na_2C_2$, $K_2C_2$, and $CaC_2$.

In the present disclosure, the first metal carbide can be obtained with high selectivity. The selectivity of the first metal carbide is expressed as the mass of the first metal carbide relative to the total mass of the simple substance of the first metal, compounds containing the first metal (including the first metal carbide), and carbon contained in the precipitates on the cathode. The selectivity of the first metal carbide can be 60 mass % or more, or can be 80 mass % or more. The selectivity of the first metal carbide may be 99 mass % or less, or may be 90 mass % or less. In one embodiment, the selectivity of the first metal carbide is 90 mass % or more and 99.9 mass % or less.

Examples of the compounds containing the first metal other than the first metal carbide include salts of the first metal and the second anion (for example, halides of the first metal), carbonates of the first metal, oxides of the first metal, hydrides of the first metal, and peroxides of the first metal. (Impurities)

The precipitates may contain impurities. The impurities are precipitates of substances other than the first metal carbide. Examples of the impurities contained in the precipitates on the cathode include at least one selected from the group consisting of carbon, a solidified electrolyte (other metal salt), a compound containing a metal material constituting a device such as an electrode material, minor component contained in the molten salt or the oxide of the first metal, simple substance of the first metal, a compound containing a first metal not included in the target first metal carbide, and a compound containing the second metal.

The carbon may include at least one selected from the group consisting of nanocarbon materials such as graphite, amorphous carbon, glassy carbon, carbon nanotube, diamond, nano diamond, and graphene. Examples of the compound containing the second metal include at least one selected from the group consisting of the simple substance, halide, carbonate, oxide, and carbide of the second metal. Examples of the compound containing a metal material constituting a device include at least one selected from the group consisting of the halides, oxides, carbonates, simple substance of said metal, and their hydrates.

For example, when the first metal is Li, a mixture of LiCl and KCl is used as the other metal salt, and a constituent of the device contains nickel, the precipitates may contain at least one selected from the group consisting of Li, KCl, LiCl, $Li_2CO_3$, $K_2CO_3$, $LiKC_2$, $HLiC_2$, $K_2C_2$, $NiCl_2$, as an impurity.

The amount of impurities is preferably 40 mass % or less, more preferably 20 mass % or less, particularly preferably 10 mass % or less, in all precipitates on the cathode. The amount of impurities may be 10 mass % or more, 1 mass % or more, or 0.1 mass % or more, in all precipitates. In one embodiment, the amount of impurities is 0.1 mass % or more and 10 mass % or less, in all precipitates.

The presence of the first metal carbide, the simple substance of the first metal, the compound containing the first metal, and other impurities can be confirmed and quantified, for example, by Raman spectroscopy and X-ray diffraction (XRD) analysis of the precipitates.

[Method for Producing Hydrocarbon]

Figure 2:
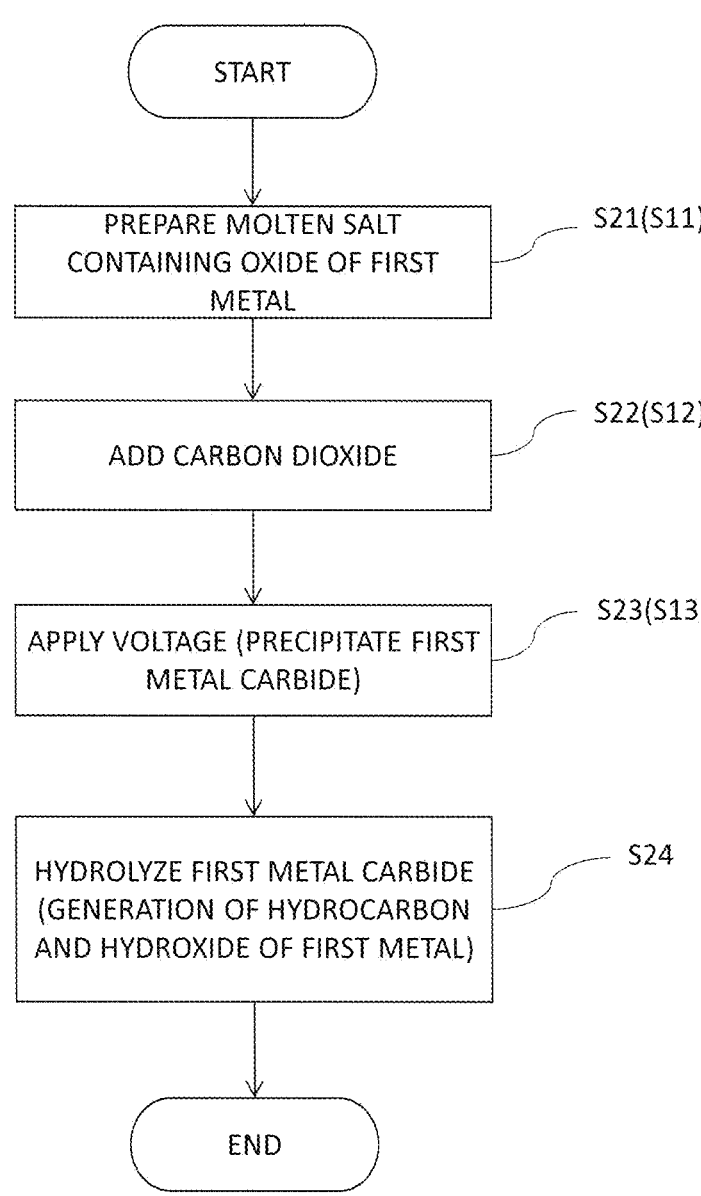
FIG. 2 is a flowchart showing a method for producing a hydrocarbon according to the present disclosure.

The present disclosure includes a method for producing a hydrocarbon from a metal carbide to be obtained using $CO_2$. The method for producing a hydrocarbon in the present disclosure comprises: preparing a molten salt containing an oxide of a first metal; adding carbon dioxide to the molten salt; applying a voltage to the molten salt containing carbon dioxide to obtain precipitates containing a carbide of the first metal; and hydrolyzing the carbide of the first metal to obtain a hydrocarbon and a hydroxide of the first metal. FIG. 2 is a flowchart showing the method for producing a hydrocarbon according to the present disclosure.

(1) Preparation of Molten Salt (S21)

In the same manner as in "Preparation of molten salt (S11)" of the method for producing a metal carbide described above, a molten salt is prepared.

(2) Addition of Carbon Dioxide (S22)

In the same manner as in "Addition of carbon dioxide (S12)" of the method for producing a metal carbide described above, $CO_2$ is added to the molten salt.

(3) Application of Voltage (S23)

In the same manner as in "Application of voltage (S13)" of the method for producing a metal carbide described above, a voltage is applied to the molten salt. This produces precipitates containing the first metal carbide.

(4) Hydrolysis of Metal Carbide (S24)

carbide isolated, or when a small amount of impurities (in particular, the simple substance of a metal) are contained in the precipitates, acetylene is obtained as a main component. The main component is a component that accounts for 50 mass % or more of the total mass of the gas to be recovered. Acetylene is an industrially important hydrocarbon.

The gas to be obtained may contain water vapor, hydrogen, nitrogen, and oxygen, as impurities, other than the hydrocarbon. The amount of impurities is preferably 10 mass % or less, more preferably 1 mass % or less, in the gas to be recovered. The amount of impurities may be 0.0001 mass % or more, or 0.001 mass % or more, in the gas to be recovered. In one embodiment, the amount of impurities is 0.0001 mass % or more and 1 mass % or less in the gas to be recovered.

The gas to be recovered, for example, may contain acetylene and at least one selected from the group consisting of ethylene, ethane, methane, and hydrogen.

The presence of the hydrocarbon and impurities can be confirmed and quantified, for example, by gas chromatograph mass spectrometry (GC-MS analysis), Fourier transform infrared absorption spectroscopy (FT-IR analysis) with gas cell, or ultraviolet-visible absorption spectroscopy (UV-Vis analysis) of the gas to be recovered.

In the present disclosure, the Faraday efficiency e for the generation of the hydrocarbon is improved. The Faraday efficiency e may be, for example, 50% or more, or 80% or more. The Faraday efficiency e may be, for example, 99.9% or less, or 99% or less. In one embodiment, the Faraday efficiency e is 50% or more and 99.9% or less.

For example, the Faraday efficiency e for the generation of $C_2H_2$ can be calculated, as follows.

First, the volume proportion of $C_2H_2$ contained in the gas recovered is calculated from the total area of the peaks obtained from the GC-MS analysis and the calibration curve. Next, the volume of $C_2H_2$ generated is calculated from the volume occupied by the gas phase in the recovery container and the volume proportion of $C_2H_2$ in each gas calculated. Finally, assuming that the $C_2H_2$ generated was in standard conditions (0° C., 101 kPa), the Faraday efficiency e (%) is calculated by the following formula.

$$e\ [\%] = \frac{\text{Actually measured amount of C2H2 produced [mol]}}{\text{Theoretical amount of C2H2 produced, determined from electrical quantity [mol]}} \times 100 =$$

$$\frac{\dfrac{\text{Calculated volume of C2H2 produced [L]}}{\text{Volume of C2H2 in standard state (224) [L/mol]}}}{\dfrac{\text{Average current value during electrolysis } [A] \times \text{electrolysis time [s]}}{\text{Faraday constant (96485) [C/mol]} \times \text{Number of electrons in C2H2 (10) [-]}}} \times 100$$

Water is brought into contact with the first metal carbide for hydrolysis. This generates a gas containing the target hydrocarbon. Hydrocarbons usually have low solubility in water. The generated hydrocarbon is rapidly exhausted into the gas phase and recovered.

The first metal carbide may be isolated from the precipitates for hydrolysis. Isolation is performed, for example, by a method of pulverizing the precipitates and using the difference in specific gravity. Alternatively, the precipitates may be hydrolyzed, as they are. The carbide of the second metal that may be contained in the precipitates is also hydrolyzed, to generate a hydrocarbon.

Examples of the hydrocarbon to be obtained include methane, ethane, ethylene, acetylene ($C_2H_2$), propane, propylene, butane, and butene. When using the first metal The amount of water to be brought into contact with the precipitates is appropriately set depending on the mass of the precipitates. The amount of water is, for example, equal to or more than the amount necessary for hydrolysis of the metal carbide and the metal contained in the precipitates. In addition, it is desirable to use the amount of water that can immerse the entire precipitates and determined in consideration of evaporation due to heat during hydrolysis. It is desirable to use an amount of water or more than that capable of dissolving all hydroxides to be generated since the hydroxide of the first metal is easily recovered. Use of an excess amount of water tends to increase the load to recover the hydroxide of the first metal. When the first metal is lithium, it may be, for example, 10 times or more, or 20 times or more the mass of the precipitates. The amount of water may be, for example, 100 times or less, or 50 times or less the mass of the precipitates.

The hydroxide of the first metal is generated by the hydrolysis of the first metal carbide together with the hydrocarbon. For example, when lithium carbide is hydrolyzed, lithium hydroxide is generated together with acetylene (Formula 9).

$$Li_2C_2 + 2H_2O \rightarrow C_2H_2 + 2LiOH \qquad \text{(Formula 9)}$$

(Recycling System)

The present disclosure further comprises recovering, as an oxide, the hydroxide of the first metal produced as a by-product during hydrolysis, to reuse for producing the first metal carbide as a metal source. This allows hydrocarbons to be produced in a cyclical method.

Figure 3:
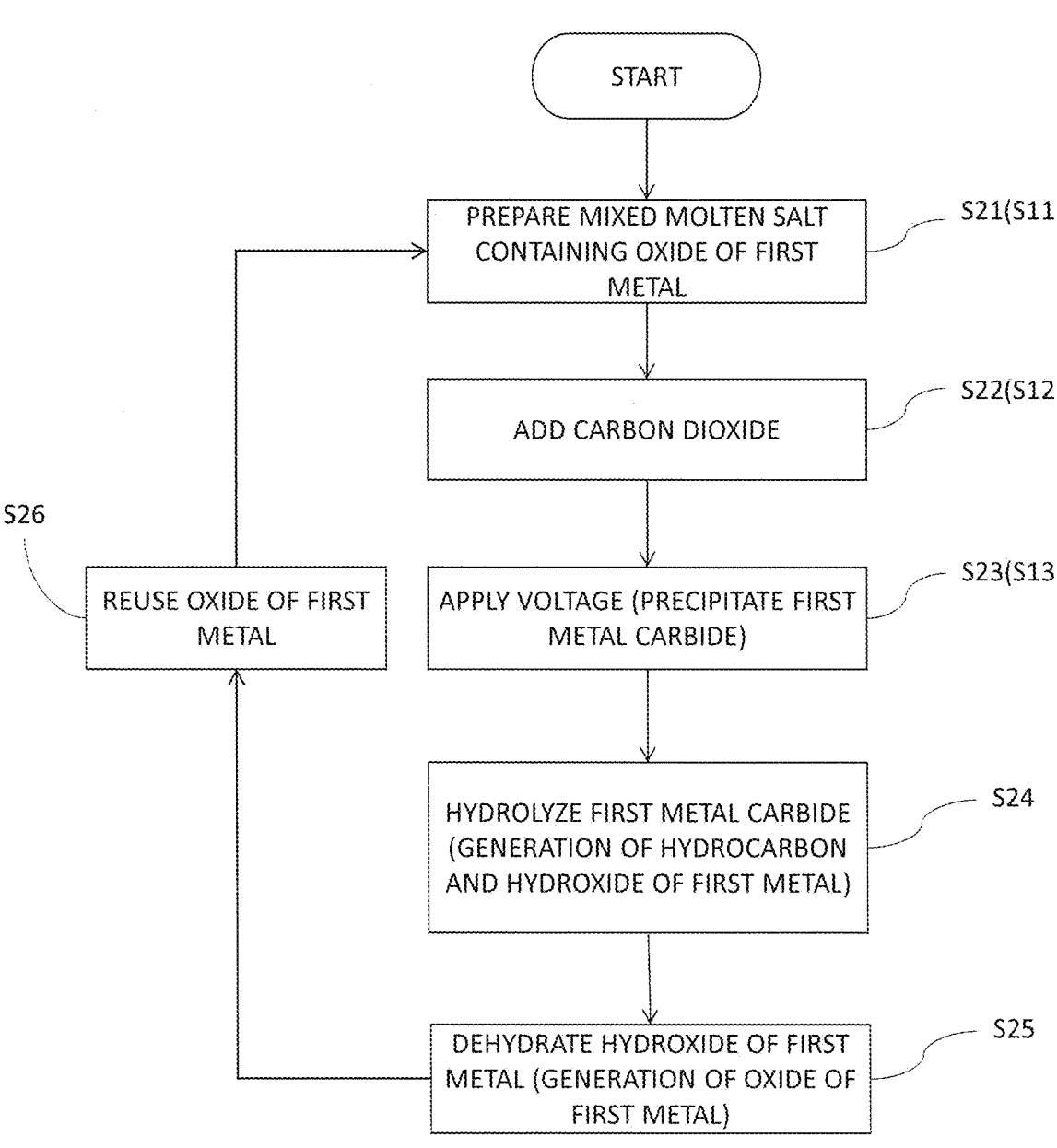
FIG. 3 is a flowchart showing another method for producing a hydrocarbon according to the present disclosure.

The method for producing a hydrocarbon of the present disclosure further comprises obtaining an oxide of the first metal by dehydrating the hydroxide of the first metal generated, and reusing the oxide of the first metal obtained for preparing the molten salt in (1) above. FIG. 3 is a flowchart showing another method for producing a hydrocarbon (recycling system) according to the present disclosure.

(5) Dehydration of Hydroxide of First Metal (S25)

The hydroxide of the first metal generated together with the hydrocarbon is dehydrated, to reproduce the oxide of the first metal.

Depending on the solubility in water, the hydroxide of the first metal is settled or dissolved in water used for hydrolysis. The impurities contained in the precipitates are also settled or dissolved in water. The impurities are desirably removed as much as possible, before the hydroxide of the first metal is dehydrated.

When the solubility S of the hydroxide of the first metal in water at 20° C. is 10 g/100 g $H_2O$ or more, (i) the impurities (typically, carbon) settled in water are first removed by filtration or centrifugation. Then, (ii) water is removed from the remaining aqueous solution by heating or the like to obtain the hydroxide of the first metal, and the hydroxide of the first metal obtained is dehydrated by heating, to produce the first metal as an oxide.

For example, the solubility S of lithium hydroxide is 12.8 g/100 g $H_2O$. When the first metal is lithium, the impurities settled are first removed by filtration. Thereafter, the filtrate is sufficiently heated, then lithium oxide is obtained by the following reaction formula.

$$2LiOH \rightarrow Li_2O + H_2O$$

Examples of the first metal with a solubility S of the hydroxide of 10 g/100 g $H_2O$ or more include sodium, potassium, rubidium, and cesium, other than lithium.

When the solubility S of the hydroxide of the first metal is 10 g/100 g $H_2O$ or more, and the solubility S of the carbonate of the first metal is ½ or less of the solubility S of the hydroxide of the first metal, the first metal may be settled as a carbonate by blowing an equivalent amount of $CO_2$ into water containing the hydroxide of the first metal. The oxide of the first metal can be obtained more efficiently by heating the sediment for pyrolysis. For example, the solubility S of lithium carbonate is 1.33 g/100 g $H_2O$, which is about ⅒ of the solubility S of lithium hydroxide. Lithium can be efficiently obtained as an oxide by once being settled as a carbonate. Lithium carbonate settled in water is pyrolyzed easily into lithium oxide by heating.

Examples of the first metal with a solubility S of the hydroxide of 10 g/100 g $H_2O$ or more and a solubility S of the carbonate of ½ or less of the solubility S of the hydroxide include lithium, sodium, potassium, calcium, strontium, and barium.

When the solubility S of the hydroxide of the first metal is less than 10 g/100 g $H_2O$, and the first metal can form a bicarbonate, the bicarbonate of the first metal may be once generated by blowing an excess amount of $CO_2$ into water containing the hydroxide of the first metal. The bicarbonate of the first metal is easily dissolved in water. Then, the sediment containing impurities is removed in the same manner as in (i) and (ii) above. The remaining aqueous solution is heated to pyrolyze the bicarbonate of the first metal and the hydroxide of the first metal is regenerated. Finally, the hydroxide of the first metal is dehydrated, to generate the first metal as an oxide.

For example, the solubility S of calcium hydroxide (Ca$(OH)_2$) is 0.17 g/100 g $H_2O$, and calcium forms a bicarbonate. Calcium oxide (CaO) can be obtained from the calcium hydroxide (Ca$(OH)_2$) by the following reaction formula, through calcium bicarbonate (Ca$(HCO_3)_2$) and calcium hydroxide (Ca$(OH)_2$).

$$Ca(OH)_2 + 2CO_2 \rightarrow Ca(HCO_3)_2$$

$$Ca(HCO_3)_2 \rightarrow Ca(OH)_2 + 2CO_2$$

$$Ca(OH)_2 \rightarrow CaO + H_2O$$

The product containing the oxide of the first metal can contain the oxide of the second metals, hydroxides, peroxides, carbonates, bicarbonates, and their hydrates of the first and second metals as impurities. The amount of impurities is preferably 20 mass % or less, more preferably 10 mass % or less, of the total amount of the product. The amount of impurities may be 0.1 mass % or more, or 1.0 mass % or more, of the total amount of the aforementioned product. In one embodiment, the amount of impurities is 0.1 mass % or more and 20 mass % or less of the total amount of the product. When the amount of impurities falls within such a range, side reactions in the reuse process (for example, precipitation process of the first metal carbide) can be easily reduced, to further improve the Faraday efficiency. The presence of the oxide of the first metal and impurities can be confirmed and quantified, for example, by Raman spectroscopy and X-ray diffraction (XRD) analysis of the precipitates.

(6) Reuse of Oxide of First Metal (S26)

The oxide of the first metal obtained is reused for preparing the molten salt of (1) above. This gives a cycle including the production of the first metal carbide using the oxide of the first metal and the production of hydrocarbons using the first metal carbide. The product, which may contain impurities, may be reused.

[Metal Carbide Composition]

The present disclosure includes a metal carbide composition. The metal carbide composition comprises a carbide of the first metal as a main component and at least one selected from the group consisting of carbon, the simple substance, halide, carbonate, oxide, hydride, and peroxide of the first metal, and the simple substance, halide, carbonate, oxide, and carbide of a metal other than the first metal. The metal carbide composition is obtained, for example, by the method for producing a metal carbide of the present disclosure. The metal carbide composition is a precipitate generated on the cathode. Examples of the metal other than the first metal include the second metal.

The main component of the metal carbide composition is the carbide of the first metal. The first metal is as described above. The main component means a component that accounts for 50 mass % or more of the total mass of the metal carbide composition. The content ratio of the first metal carbide is preferably 80 mass % or more, more preferably 90 mass % or more, of the mass of the metal carbide composition. The content ratio of the first metal carbide may be 99.9 mass % or less, or 99 mass % or less, of the mass of the metal carbide composition. In one embodiment, the content ratio of the first metal carbide is 80 mass % or more and 99.9 mass % or less of the mass of the metal carbide composition.

Also when the metal carbide composition is obtained by the method for producing a metal carbide of the present disclosure, the metal carbide composition contains at least one selected from the group consisting of carbon, the simple substance, halide, carbonate, oxide, hydride, and peroxide of the first metal, and the simple substance, halide, carbonate, oxide, and carbide of the second metal, together with the first metal carbide. Other than above, the metal carbide composition may contain at least one selected from the group consisting of a solidified electrolyte (other metal salt), the halide, oxide, metal of the material constituting a device, and their hydrates. The carbon may contain at least one selected from the group consisting of a nanocarbon material such as graphite, amorphous carbon, glassy carbon, carbon nanotube, diamond, nanodiamond, and graphene.

EXAMPLES

Example 1

(Production of Metal Carbide)

LiCl and KCl were mixed so as to be LiCl/KCl=58.5 mol %/41.5 mol %, followed by vacuum drying at 200° C., 100 Pa or less for 24 hours or more. 5 mol % of Li$_2$O relative to the total number of moles of LiCl and KCl was weighed, and a mixed salt was obtained in addition to the mixture. The mixed salt was accommodated in four containers made of glass and set in an electric furnace, to heat the mixed salt to 450° C. Thus, a molten salt of LiCl—KCl—Li$_2$O was obtained.

Then, a working electrode (nickel plate of 1 cm×1.5 cm), a counter electrode (platinum coil), and a reference electrode (Ag$^+$/Ag) were attached to the lid of each of these containers, and the containers were sealed with the lids. CO$_2$ was blown in at a flow rate of 100 mL/minute for 30 minutes or more into the molten salt in each of the four containers at 450° C. Subsequently, a voltage was applied, while the potential of the working electrode relative to the reference electrode was maintained at 0.09 V using a potentio-galvanostat. The application times were 10 minutes, 30 minutes, 1 hour, and 2 hours, respectively. Precipitates were confirmed on the working electrode. All experimental operations were performed in a glovebox containing a high-purity argon atmosphere.

(Production of Hydrocarbon)

The precipitates were respectively accommodated in four sealed test tubes. A small amount of pure water was added to each of these test tubes at normal temperature (23° C.), so that the precipitates was hydrolyzed. The total amount of water added was 2.5 ml each. Bubbling was confirmed in the test tubes, and then the test tubes were left standing until no bubbling was observed. Subsequently, 100 µl (micro liter) of the gas in the test tube was collected using a gastight syringe.

The gas obtained were subjected to GC-MS analysis using a gas chromatograph (GC) device, and the GC-MS analysis demonstrated C$_2$H$_2$ was generated as the main component. Furthermore, it revealed that methane, ethane, and hydrogen were generated as by-products. Other than above, water, carbon dioxide, nitrogen, oxygen, and argon were contained as impurities. In addition, the amount of each component generated was confirmed. The mass proportion of C$_2$H$_2$ in the recovered gas was sufficiently greater than 50 mass %.

Figure 4A:
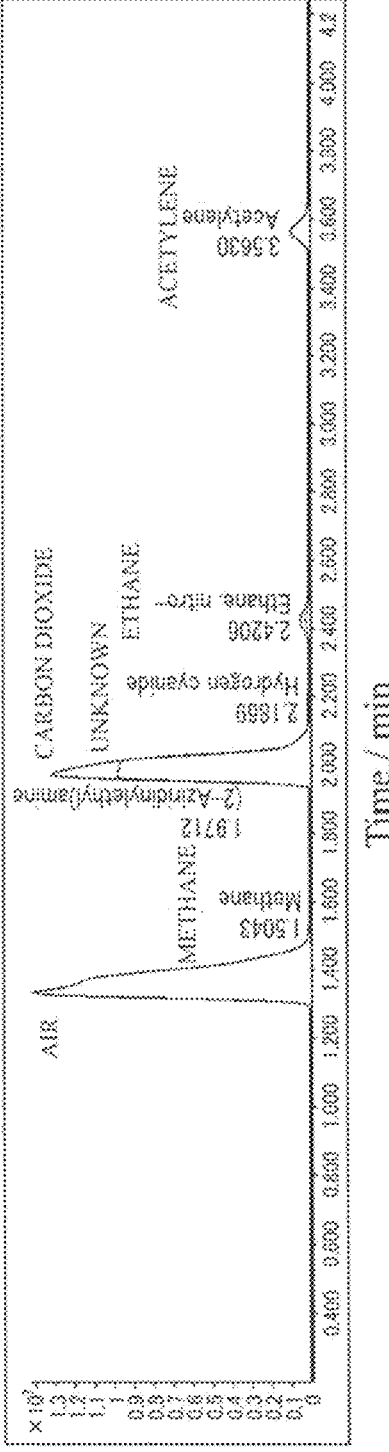
FIG. 4A is a graph showing a part of the results of the GC-MS analysis of the hydrolysate obtained in Example 1.

FIG. 4A is the results of the GC-MS analysis of the gas obtained by applying a voltage for 1 hour to hydrolyze the precipitates obtained. The Faraday efficiency for the C$_2$H$_2$ gas generation was calculated to be about 25.2%. The average of the current at this time was 359.4 mA.

Figure 4B:
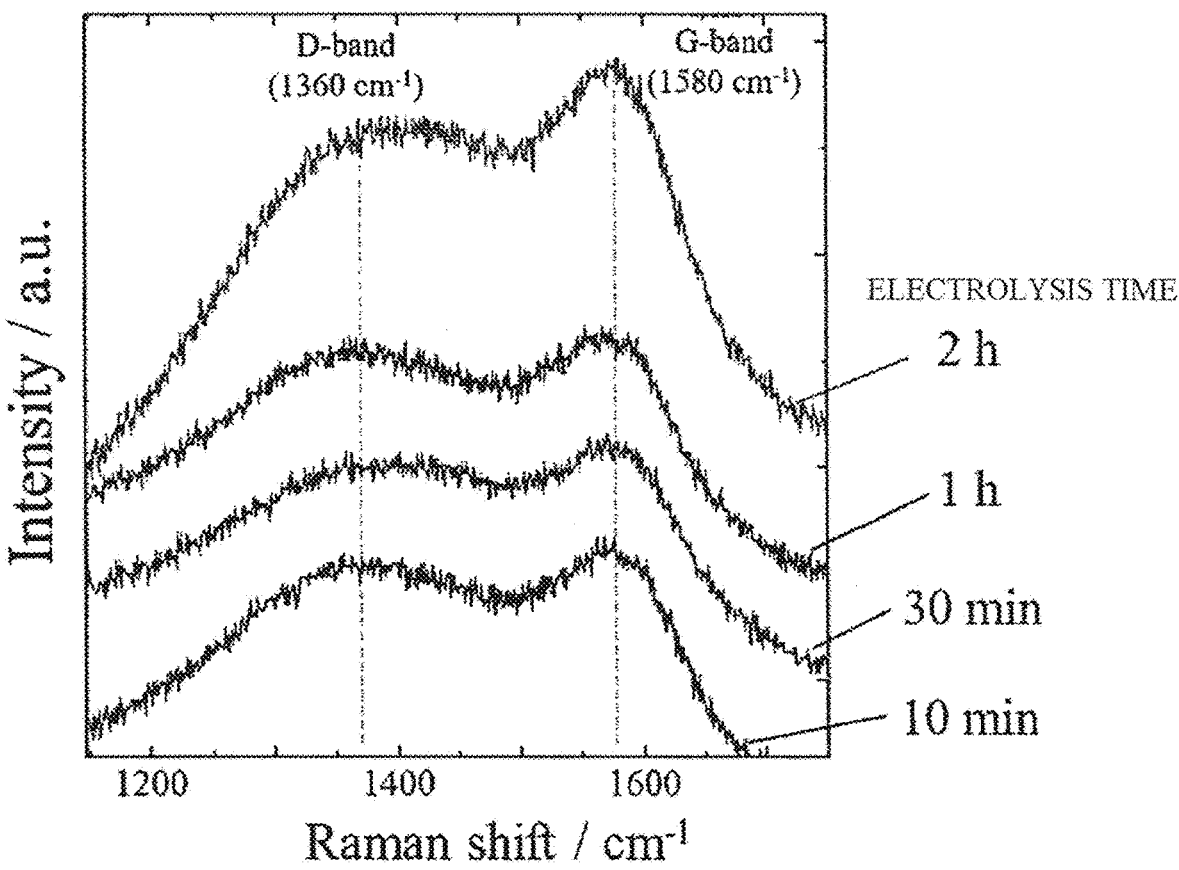
FIG. 4B is a graph showing the results of the Raman spectroscopy of the hydrolysate obtained in Example 1.
Figure 4C:
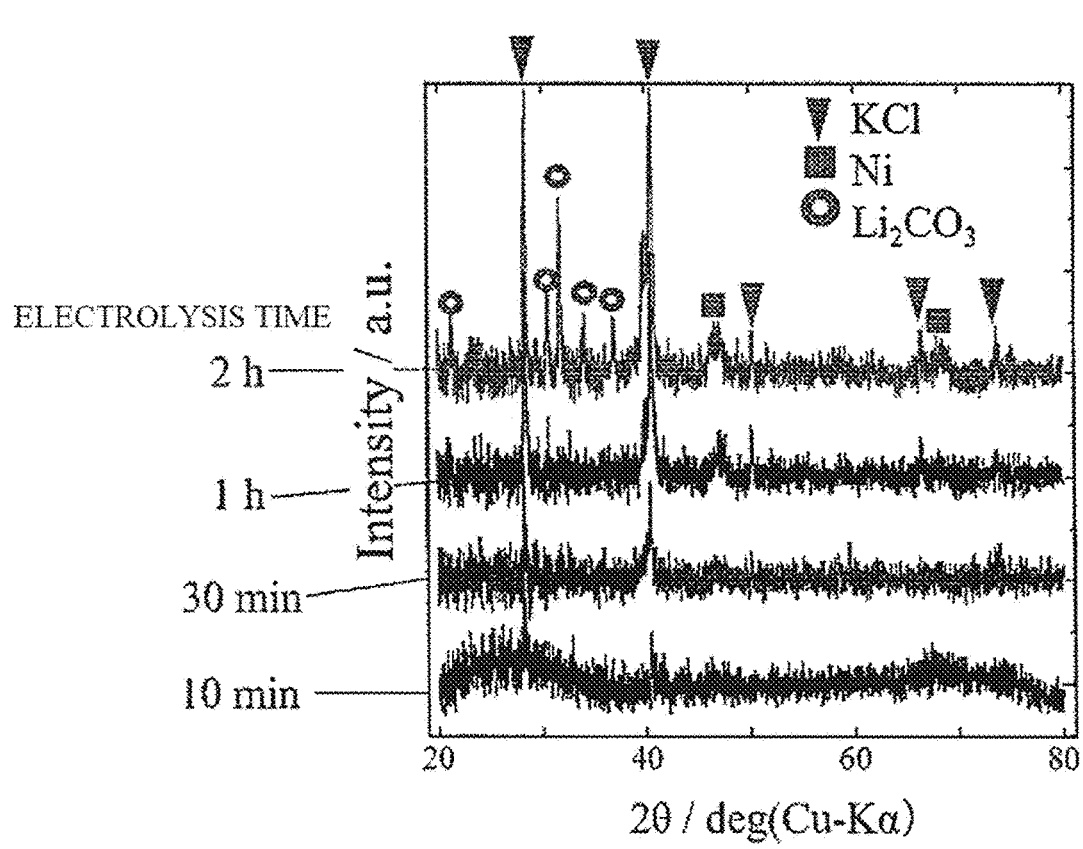
FIG. 4C is a graph showing the results of the XRD analysis of the hydrolysate obtained in Example 1.

The four hydrolysates were each subjected to the Raman spectroscopy and XRD analysis. FIG. 4B and FIG. 4C show the analysis results. FIG. 4B and FIG. 4C collectively show the analysis results of the precipitates obtained by setting a voltage application time to 10 minutes, 30 minutes, 1 hour, and 2 hours. These analyses demonstrated that all hydrolysates contained at least KCl, Ni, carbon, and Li$_2$CO$_3$. Therefore, the precipitates before the hydrolysis are considered to contain the KCl, Ni, carbon, and Li$_2$CO$_3$ described above together with Li$_2$C$_2$. The mass proportion of the impurity in the hydrolysate was sufficiently less than 50 mass %.

(Reproduction of Metal Oxide)

The liquid remaining after the hydrolysis was filtered, to remove the sediment. Then, the filtrate was sufficiently heated to dehydrate and remove water, and solidified matter was obtained. The solidified matter was subjected to XRD analysis, to confirm the reproduction of Li$_2$O as the main component. The sediment obtained by the filtration was dried and subjected to Raman spectroscopy and XRD analysis. These analyses demonstrated that the sediment contained carbon as the main component and a trace amount of nickel.

Example 2

(Production of Metal Carbide)

Figure 5:
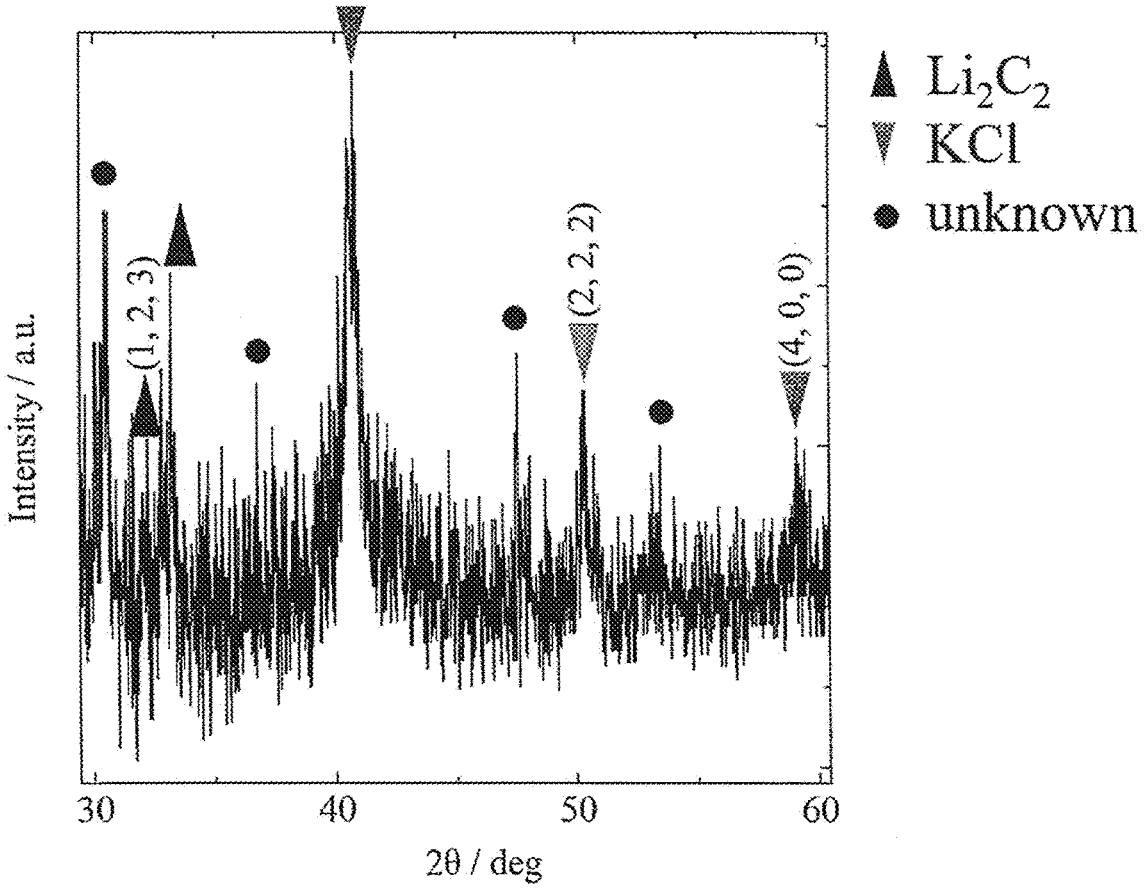
FIG. 5 is a graph showing the results of the XRD analysis of the precipitates obtained in Example 2.

Precipitates were obtained in the same manner as in Example 1, except that a voltage was applied for 30 minutes, while the potential of the working electrode relative to the reference electrode was maintained at 0.225 V. The average of the current at this time was 570 mA. The XRD analysis of the precipitates obtained demonstrated that the precipitates contained Li$_2$C$_2$, and at least KCl, LiCl, Ni, carbon, Li$_2$O, and Li$_2$CO$_3$, as an impurity. FIG. 5 shows the results of the XRD analysis of the precipitates obtained. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained C$_2$H$_2$ as the main component. Furthermore, it revealed that ethane and hydrogen were generated as by-products. Other than above, water, carbon dioxide, nitrogen, oxygen, and argon were contained as impurities. The mass proportion of C$_2$H$_2$ in the recovered gas was sufficiently greater than 50 mass %.

(Reproduction of Metal Oxide)

A solidified matter was obtained in the same manner as in Example 1. The XRD analysis of the solidified matter obtained demonstrated that the solidified matter contained $Li_2O$ as the main component.

Example 3

(Production of Metal Carbide)

Precipitates were obtained in the same manner as in Example 1, except that a voltage was applied for 1 hour, while the potential of the working electrode relative to the reference electrode was maintained at 0.3 V. The average of the current at this time was 684 mA. The results of the Raman spectroscopy and XRD analysis of the precipitates obtained demonstrated that the precipitates contained $Li_2C_2$ and at least KCl, LiCl, Ni, carbon, $Li_2O$, and $Li_2CO_3$, as an impurity. The mass proportion of the impurity in the precipitates was sufficiently less than 50 mass %.

(Production of Hydrocarbon)

Figure 6:
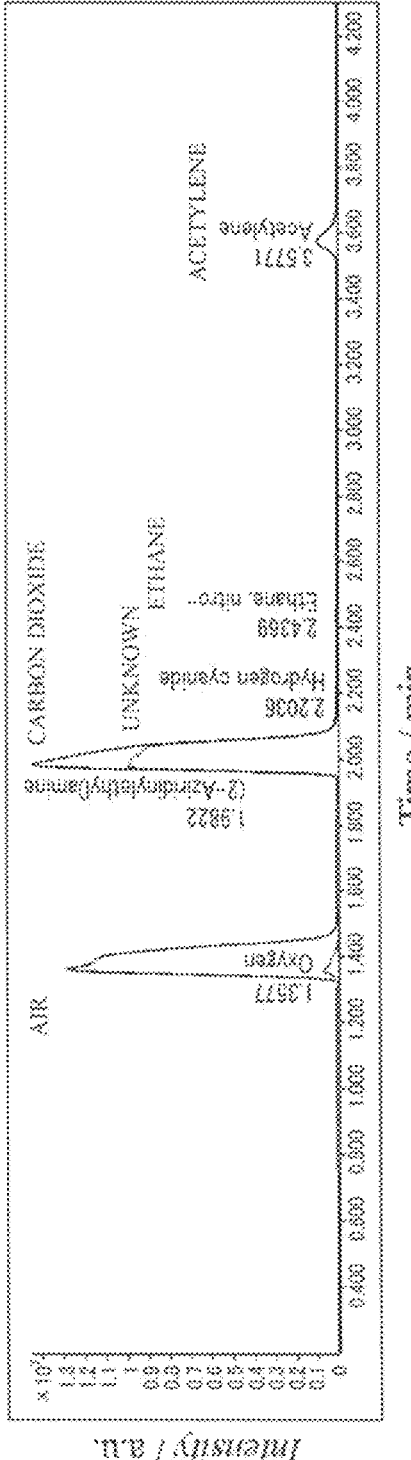
FIG. 6 is a graph showing a part of the results of the GC-MS analysis of the hydrolysate obtained in Example 3.

The precipitates were hydrolyzed in the same manner as in Example 1. The GC-MS analysis demonstrated that the gas generated contained $C_2H_2$ as the main component. FIG. 6 shows the results of the GC-MS analysis. Furthermore, it revealed that ethane and hydrogen were generated as by-products. Other than above, water, carbon dioxide, nitrogen, oxygen, and argon were contained as impurities. The mass proportion of $C_2H_2$ in the recovered gas was sufficiently greater than 50 mass %. The Faraday efficiency for the $C_2H_2$ gas generation was calculated to be about 54.7%.

(Reproduction of Metal Oxide)

A solidified matter was obtained in the same manner as in Example 1. The XRD analysis of the solidified matter obtained demonstrated that the solidified matter contained $Li_2O$ as the main component.

Example 4

(Production of Metal Carbide)

Precipitates were obtained in the same manner as in Example 1, except that a voltage was applied for 1 hour, while the potential of the working electrode relative to the reference electrode was maintained at 0.75 V. The average of the current at this time was 75 mA. The Raman spectroscopy and XRD analysis of the precipitates obtained demonstrated that the precipitates contained $Li_2C_2$ and at least KCl, LiCl, Ni, carbon, $Li_2O$, and $Li_2CO_3$, as an impurity. The mass proportion of the impurity in the precipitates was sufficiently less than 50 mass %.

(Production of Hydrocarbon)

Figure 7:
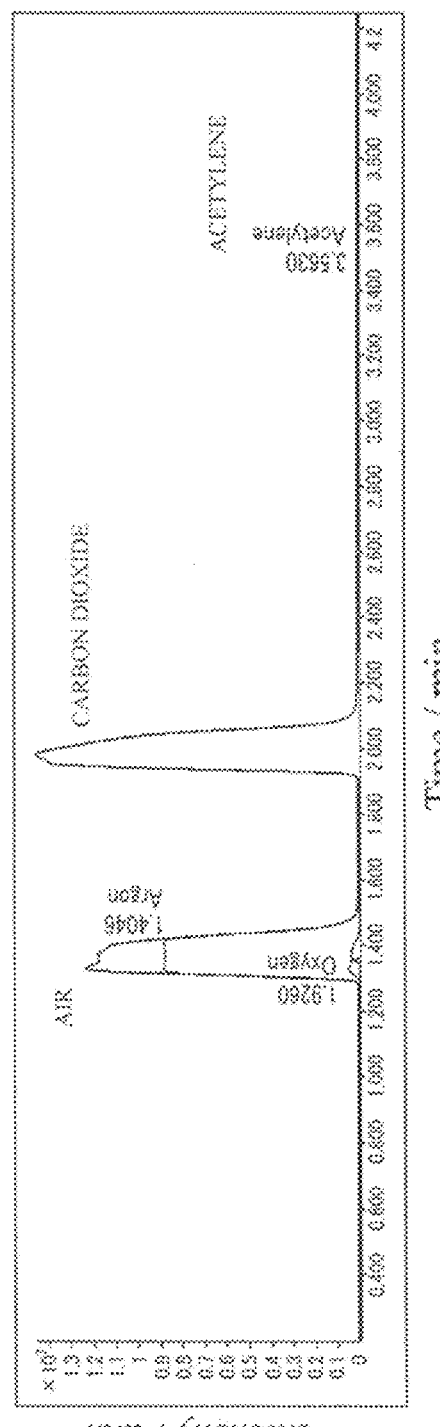
FIG. 7 is a graph showing a part of the results of the GC-MS analysis of the hydrolysate obtained in Example 4.

The precipitates were hydrolyzed in the same manner as in Example 1. The GC-MS analysis demonstrated that the gas generated contained $C_2H_2$. FIG. 7 shows a part of the results of the GC-MS analysis.

(Reproduction of Metal Oxide)

A solidified matter was obtained in the same manner as in Example 1. The XRD analysis of the solidified matter obtained demonstrated that the solidified matter contained $Li_2O$ as the main component.

Example 5

(Production of Metal Carbide)

LiCl, KCl, and $CaCl_2$ were mixed at LiCl/KCl/$CaCl_2$=52.3 mol %/11.6 mol %/36.1 mol %. 3 mol % of CaO relative to the total number of moles of LiCl, KCl, and $CaCl_2$ was weighed and added to the mixture, to obtain a mixed salt. The mixed salt was accommodated in a container and set in an electric furnace, to heat the mixed salt to 450° C. Thus, a molten salt of LiCl—KCl—$CaCl_2$—CaO was obtained.

Figure 8:
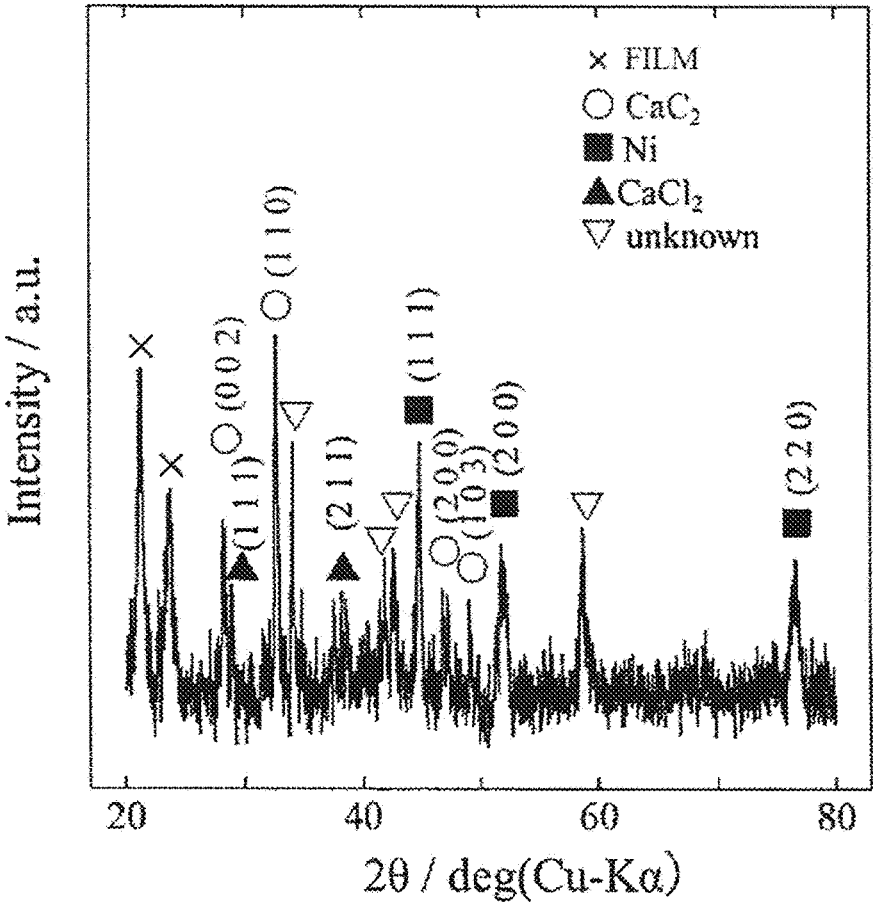
FIG. 8 is a graph showing the results of the XRD analysis of the precipitates obtained in Example 5.

Precipitates were obtained in the same manner as in Example 1, except that this molten salt was used, and a voltage was applied for 30 minutes, while the potential of the working electrode relative to the reference electrode was maintained at 0.4 V. The Raman spectroscopy and XRD analysis of the precipitates obtained demonstrated that the precipitates contained $CaC_2$ and at least LiCl, KCl, $CaCl_2$, Ni, carbon, CaO, and $CaCO_3$, as an impurity. FIG. 8 shows the results of the XRD analysis of the precipitates obtained. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$ as the main component. Furthermore, it revealed that ethane and hydrogen were generated as by-products. Other than above, water, carbon dioxide, nitrogen, oxygen, and argon were contained as impurities. The mass proportion of $C_2H_2$ in the recovered gas was sufficiently greater than 50 mass %.

(Reproduction of Metal Oxide)

$CO_2$ was blown into the liquid remaining after the hydrolysis. Then, the sediment was removed by filtration. The filtrate was sufficiently heated to dehydrate and remove water, and solidified matter was obtained. The XRD analysis of the solidified matter obtained demonstrated that the solidified matter contained CaO as the main component.

Example 6

(Production of Metal Carbide)

Precipitates were obtained in the same manner as in Example 5, except that a voltage was applied for 1 hour, while the potential of the working electrode relative to the reference electrode was maintained at 0.15 V. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

Figure 9:
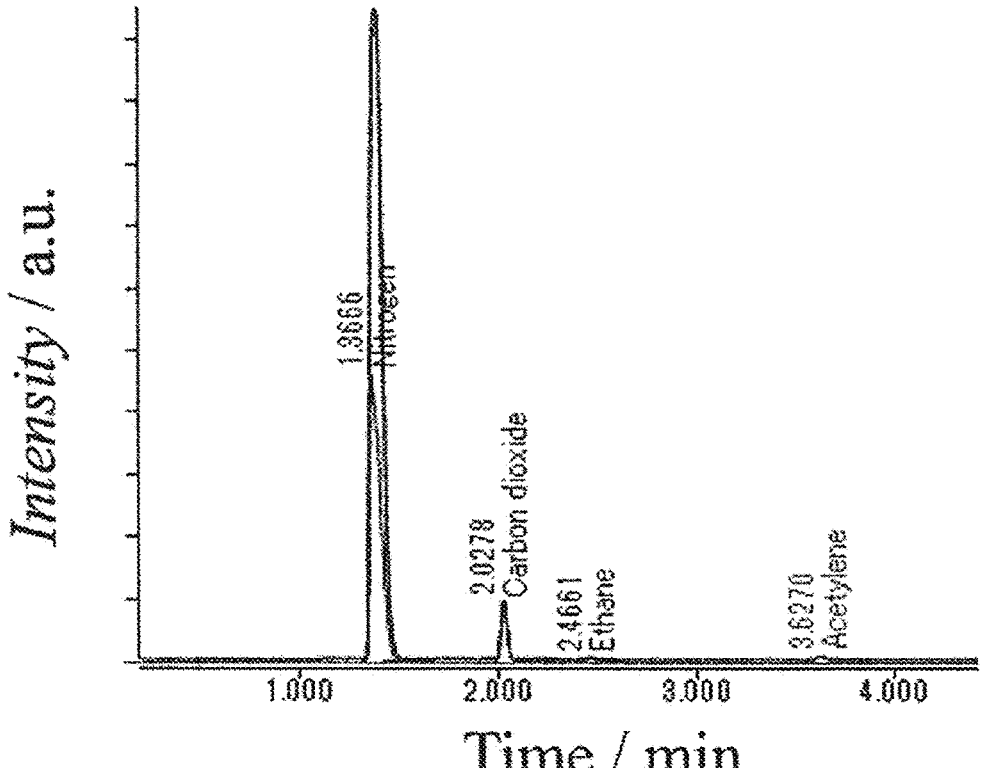
FIG. 9 is a graph showing the results of the GC-MS analysis of the hydrolysate obtained in Example 6.

The precipitates were hydrolyzed in the same manner as in Example 1. The GC-MS analysis demonstrated that the gas generated contained $C_2H_2$. Furthermore, it revealed that ethane and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. FIG. 9 shows the results of the GC-MS analysis.

(Reproduction of Metal Oxide)

A solidified matter was obtained in the same manner as in Example 5. The XRD analysis of the solidified matter obtained demonstrated that the solidified matter contained CaO as the main component.

Example 7

(Production of Metal Carbide)

Precipitates were obtained in the same manner as in Example 5, except that iron was used as the working electrode, and a voltage was applied for 2 hours, while the potential of the working electrode relative to the reference electrode was maintained at 0.80 V. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

Figure 10:
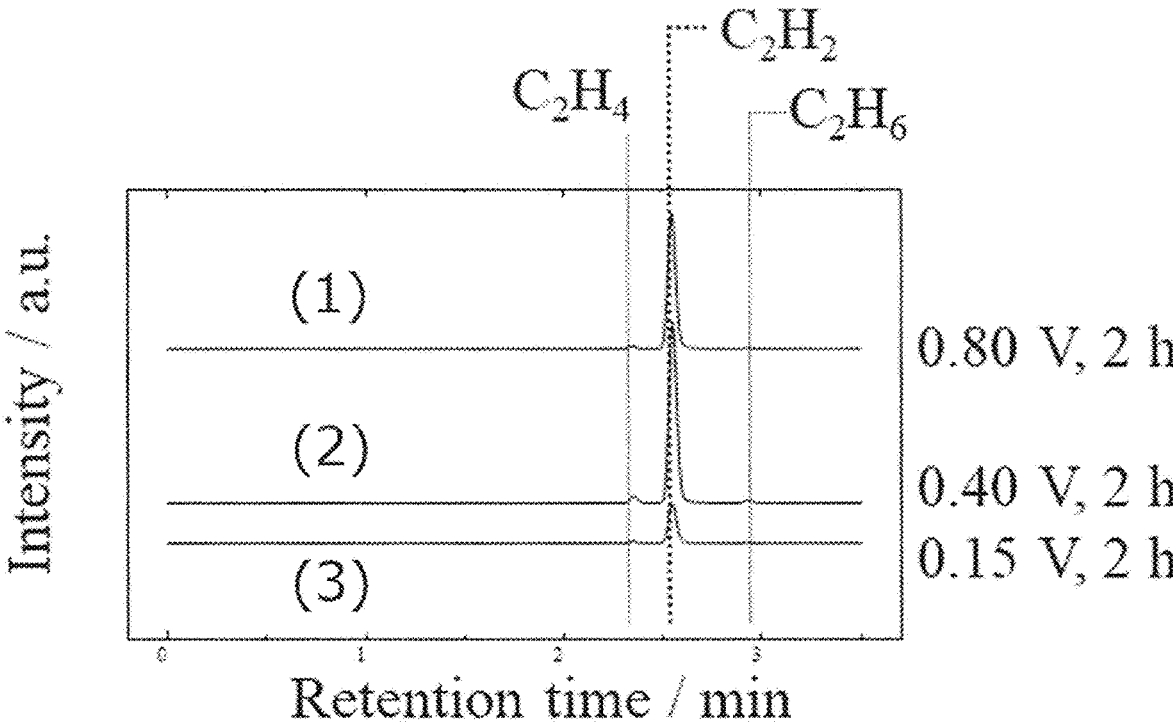
FIG. 10 is a graph showing the results of the GC-MS analysis of the gas generated in Examples 7 to 9.

The precipitates were hydrolyzed in the same manner as in Example 1. The GC-MS analysis demonstrated that the gas generated contained $C_2H_2$. Furthermore, it revealed that ethylene and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. FIG. 10(1) shows the results of the GC-MS analysis.

(Reproduction of Metal Oxide)

A solidified matter was obtained in the same manner as in Example 5. The XRD analysis of the solidified matter obtained demonstrated that the solidified matter contained CaO as the main component.

Example 8

(Production of Metal Carbide)

Precipitates were obtained in the same manner as in Example 5, except that the potential of the working electrode relative to the reference electrode was maintained at 0.40V. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. FIG. 10(2) shows the results of the GC-MS analysis.

(Reproduction of Metal Oxide)

A solidified matter was obtained in the same manner as in Example 5. The XRD analysis of the solidified matter obtained demonstrated that the solidified matter contained CaO as the main component.

Example 9

(Production of Metal Carbide)

Precipitates were obtained in the same manner as in Example 5, except that the potential of the working electrode relative to the reference electrode was maintained at 0.15 V. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. FIG. 10(3) shows the results of the GC-MS analysis.

(Reproduction of Metal Oxide)

A solidified matter was obtained in the same manner as in Example 5. The XRD analysis of the solidified matter obtained demonstrated that the solidified matter contained CaO as the main component.

Example 10

(Production of Metal Carbide)

Precipitates were obtained in the same manner as in Example 5, except that energization was performed until the energization quantity reached 100 C, while the current value between the working electrode and the counter electrode was maintained at $-100$ mA, that is, the current density was maintained at $-50$ mA/cm$^2$.

Figure 11:
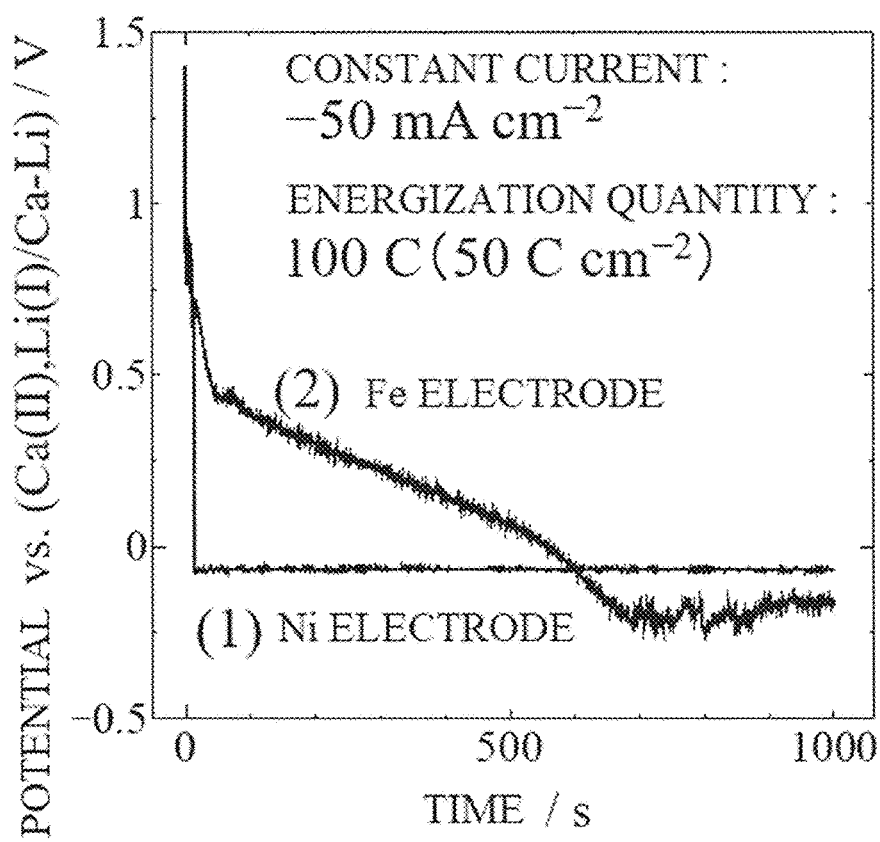
FIG. 11 is a graph showing the potential change of the working electrode relative to the reference electrode during energization for producing a metal carbide in Example 10.
Figure 12:
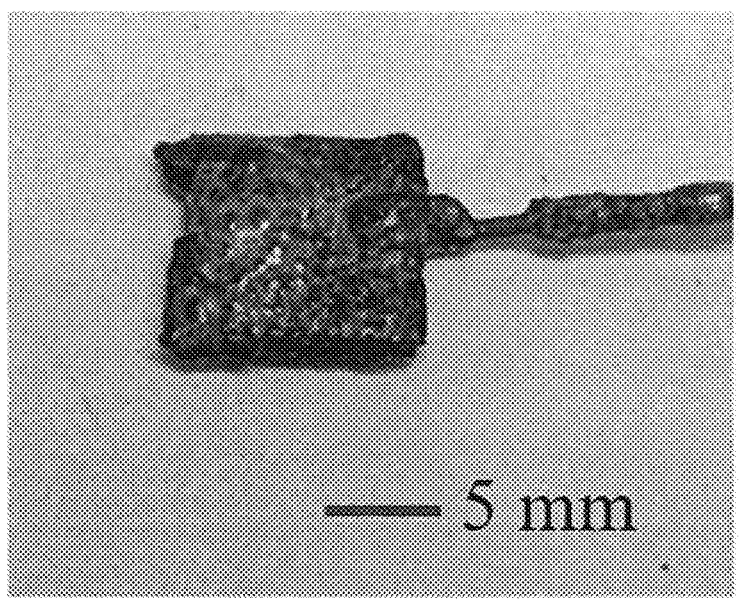
FIG. 12 is a photograph showing the appearance of the working electrode after energization for producing a metal carbide in Example 10.

FIG. 11(1) shows the potential change of the working electrode relative to the reference electrode during energization. FIG. 12 shows the appearance of the working electrode after energization. Black precipitates could be observed on the surface of the working electrode. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The Faraday efficiency for the $C_2H_2$ gas generation was calculated to be about 0.1%.

(Reproduction of Metal Oxide)

A solidified matter was obtained in the same manner as in Example 5. The XRD analysis of the solidified matter obtained demonstrated that the solidified matter contained CaO as the main component.

Example 11

(Production of Metal Carbide)

Figure 13:
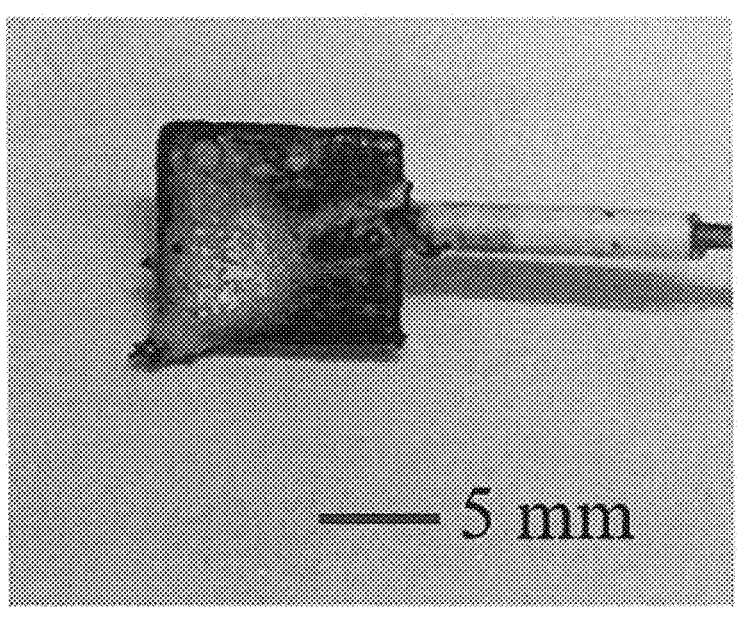
FIG. 13 is a photograph showing the appearance of the working electrode after energization for producing a metal carbide in Example 11.

Precipitates were obtained in the same manner as in Example 10 except that iron was used as the working electrode. FIG. 11(2) shows the potential change of the working electrode relative to the reference electrode during energization. FIG. 13 shows the appearance of the working electrode after energization. Black precipitates could be observed on the surface of the working electrode. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 7.9%.

(Reproduction of Metal Oxide)

A solidified matter was obtained in the same manner as in Example 5. The XRD analysis of the solidified matter obtained demonstrated that the solidified matter contained CaO as the main component.

Example 12

(Production of Metal Carbide)

NaCl, KCl, and $CaCl_2$ were mixed at NaCl/KCl/$CaCl_2$=33.4 mol %/11.6 mol %/55.0 mol %, followed by vacuum drying at 200° C. and 100 Pa or less for 24 hours or more. 3 mol % of CaO relative to the total number of moles of NaCl, KCl, and $CaCl_2$ was weighed and added to the mixture, to obtain a mixed salt. The mixed salt was accommodated in a PYREX (trademark of Corning Incorporated) container and set in an electric furnace, to heat the mixed salt to 550° C. Thus, a molten salt of NaCl—KCl—$CaCl_2$—CaO was obtained.

Figure 14:
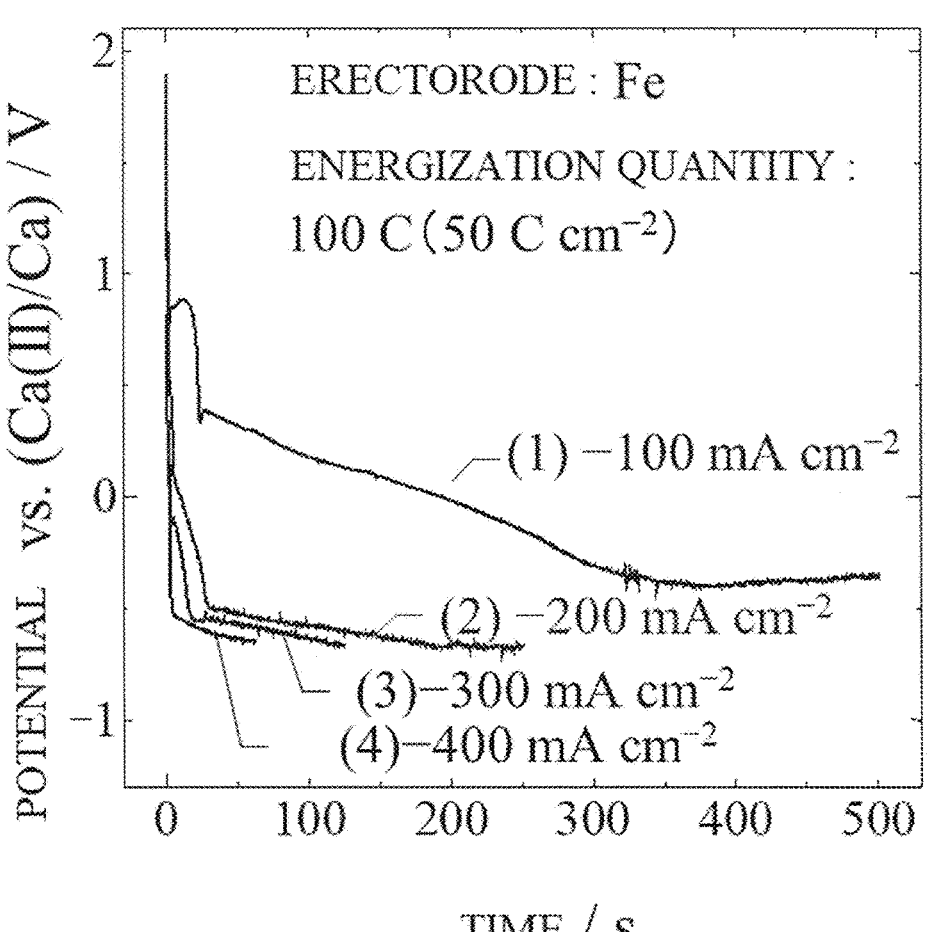
FIG. 14 is a graph showing the potential change of the working electrode relative to the reference electrode during energization for producing a metal carbide in Examples 12 to 15.

Precipitates were obtained in the same manner as in Example 11, except that this molten salt was used, and the current density was maintained at −100 mA/cm². FIG. 14(1) shows the potential change of the working electrode relative to the reference electrode during energization. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 25%.

(Reproduction of Metal Oxide)

A solidified matter was obtained in the same manner as in Example 5. The XRD analysis of the solidified matter obtained demonstrated that the solidified matter contained CaO as the main component.

Example 13

(Production of Metal Carbide)

Figure 15:
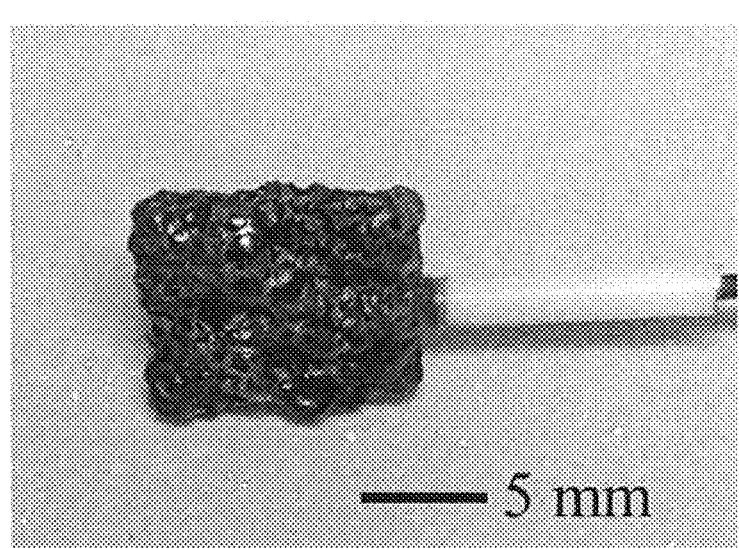
FIG. 15 is a photograph showing the appearance of the working electrode after energization for producing a metal carbide in Example 13.

Precipitates were obtained in the same manner as in Example 12, except that the current density was maintained at −200 mA/cm². FIG. 14(2) shows the potential change of the working electrode relative to the reference electrode during energization. FIG. 15 shows the appearance of the working electrode after energization. Black precipitates could be observed on the surface of the working electrode. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 34%.

(Reproduction of Metal Oxide)

A solidified matter was obtained in the same manner as in Example 5. The XRD analysis of the solidified matter obtained demonstrated that the solidified matter contained CaO as the main component.

Example 14

(Production of Metal Carbide)

Precipitates were obtained in the same manner as in Example 12, except that the current density was maintained at −300 mA/cm². FIG. 14(3) shows the potential change of the working electrode relative to the reference electrode during energization. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 22%.

(Reproduction of Metal Oxide)

A solidified matter was obtained in the same manner as in Example 5. The XRD analysis of the solidified matter obtained demonstrated that the solidified matter contained CaO as the main component.

Example 15

(Production of Metal Carbide)

Precipitates were obtained in the same manner as in Example 12, except that the current density was maintained at −400 mA/cm². FIG. 14(4) shows the potential change of the working electrode relative to the reference electrode during energization. The Raman spectroscopy and XRD analysis of the precipitates obtained demonstrated that the precipitates contained $CaC_2$, and at least $CaCl_2$ as an impurity. The mass proportion of the impurity in the precipitates was sufficiently less than 50 mass %.

(Production of Hydrocarbon)

The precipitates were hydrolyzed in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 8%.

(Reproduction of Metal Oxide)

A solidified matter was obtained in the same manner as in Example 5. The XRD analysis of the solidified matter obtained demonstrated that the solidified matter contained CaO as the main component.

Example 16

(Production of Metal Carbide)

Precipitates were obtained in the same manner as in Example 13, except that a molten salt obtained by adding 7 mol % of $CaC_2$ relative to the total number of moles of NaCl, KCl, and $CaCl_2$ in advance to the molten salt of NaCl— KCl—$CaCl_2$—CaO was used.

Figure 16:
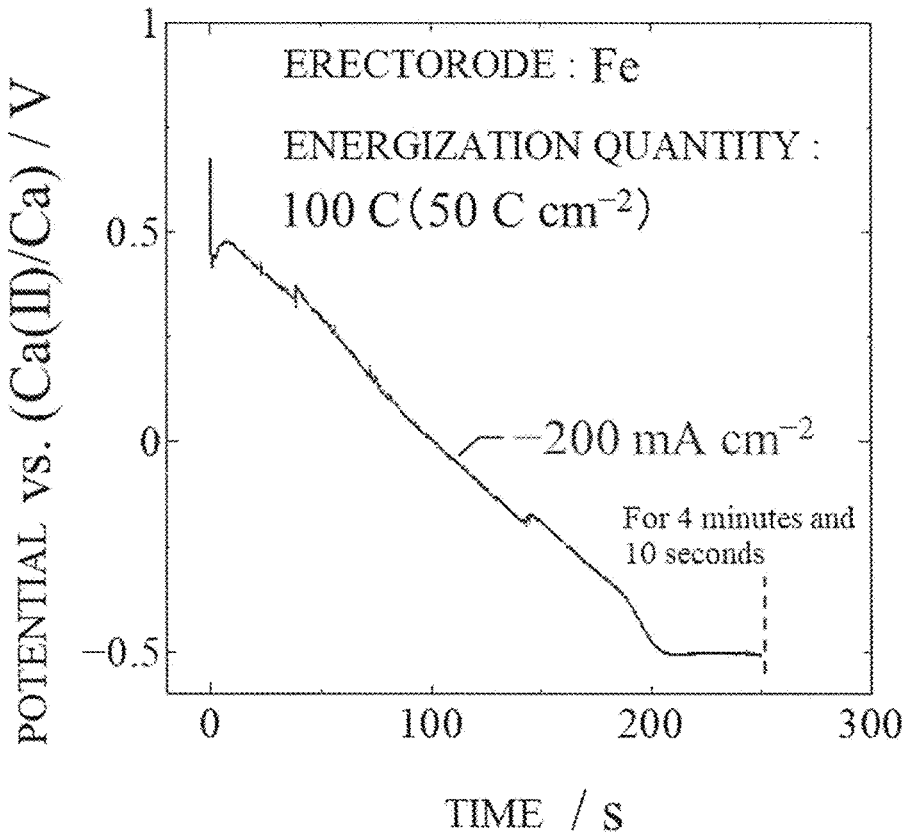
FIG. 16 is a graph showing the potential change of the working electrode relative to the reference electrode during energization for producing a metal carbide in Example 16.
Figure 17:
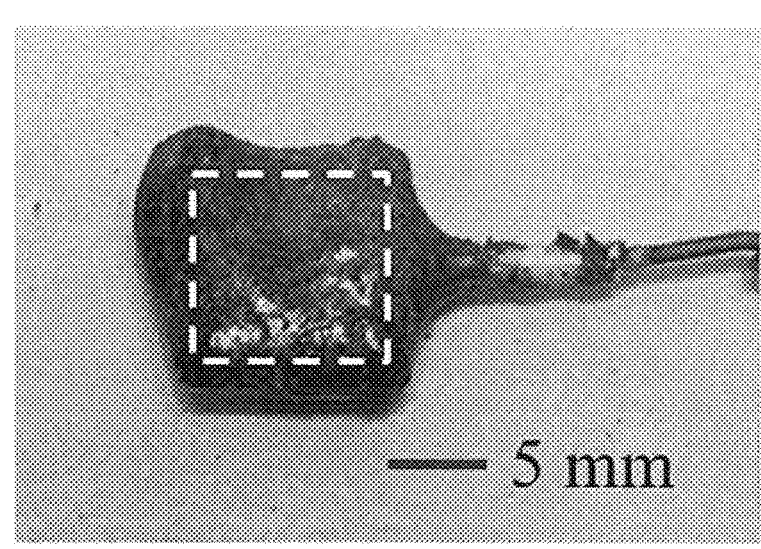
FIG. 17 is a photograph showing the appearance of the working electrode after energization for producing a metal carbide in Example 16.
Figure 18:
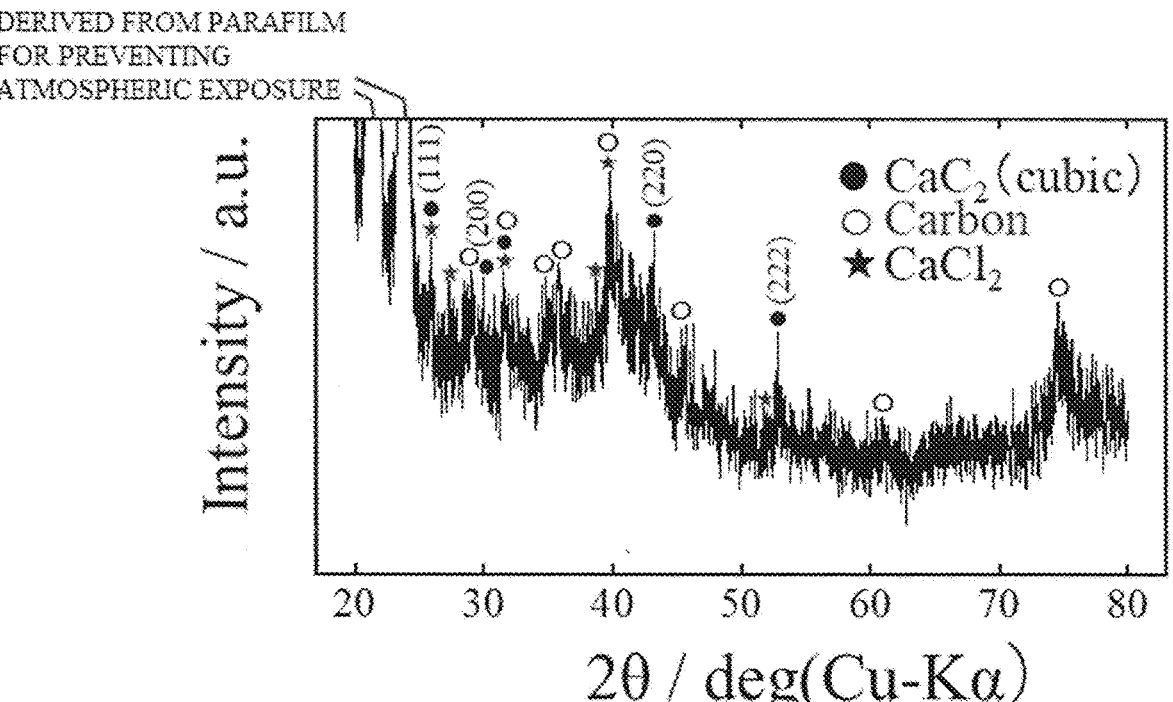
FIG. 18 is a graph showing the results of the XRD analysis of the precipitates obtained in Example 16.

FIG. 16 shows the potential change of the working electrode relative to the reference electrode during energization. FIG. 17 shows the appearance of the working electrode after energization. Black precipitates could be observed on the surface of the working electrode. The amount of precipitation was large, to increase the overall size of the working electrode due to the precipitates. FIG. 17 shows the original size of the working electrode by a dashed line for reference. FIG. 18 shows the results of the XRD analysis of the precipitates obtained. FIG. 18 demonstrated that the precipitates contained $CaC_2$, and at least carbon and $CaCl_2$ as an impurity. The mass proportion of the impurity in the precipitates was sufficiently less than 50 mass %.

(Production of Hydrocarbon)

About 1 cc of water was added to the precipitates for hydrolysis in the same manner as in Example 1. The GC-MS analysis demonstrated that the gas generated contained $C_2H_2$. Furthermore, it revealed that ethane, ethylene, and hydrogen were generated as by-products. Other than above, water, carbon dioxide, nitrogen, oxygen, and argon were generated as impurities. The mass proportion of $C_2H_2$ in the recovered gas was sufficiently greater than 50 mass %. The Faraday efficiency for the $C_2H_2$ gas generation was calculated to be about 68%. It is considered because, since a molten salt obtained by adding $CaC_2$ to the molten salt in advance was used, the dissolution of $CaC_2$ precipitated on the electrode into the molten salt was reduced.

(Reproduction of Metal Oxide)

Figure 19:
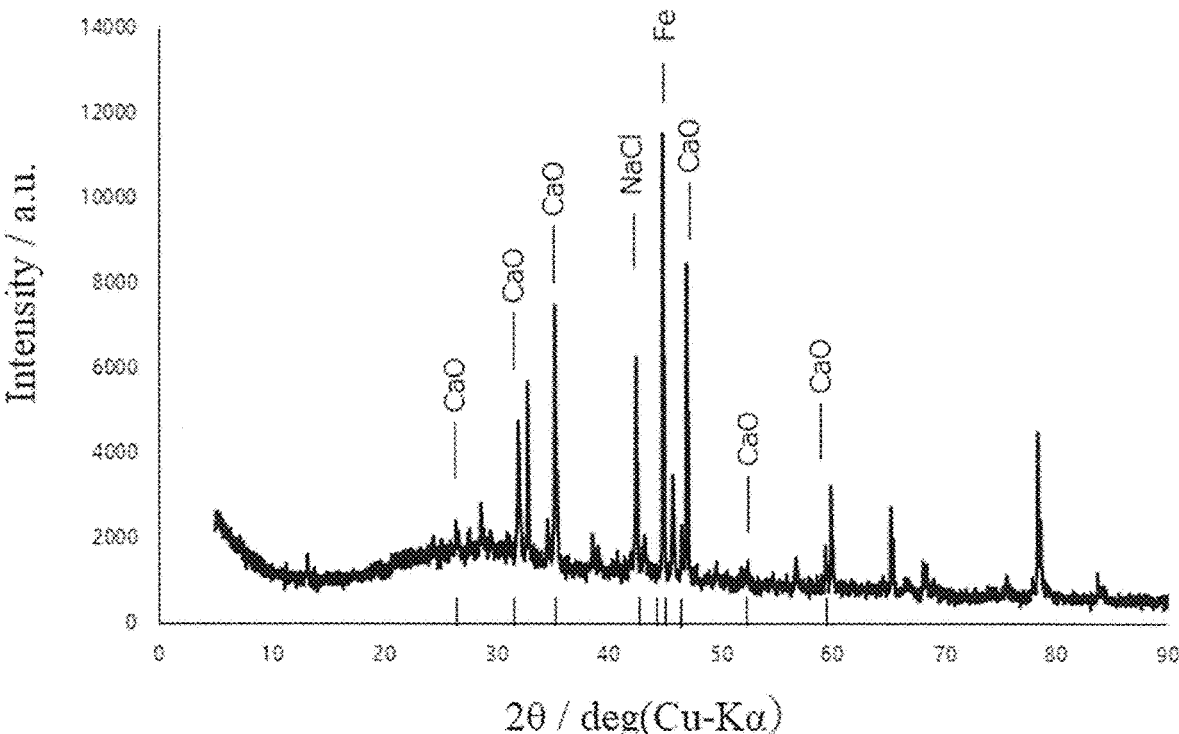
FIG. 19 is a graph showing the results of the XRD analysis of the metal oxide reproduced in Example 16.

1.14 g of an aqueous solution remaining after the hydrolysis was put into an aluminum cup, heated at 80° C. for 50 minutes, then heated at 200° C. for 20 minutes, and evaporated to dryness. 0.156 g of the black solid matter obtained was accommodated in a nickel reaction tube, and the temperature was raised to 500° C. over 3 hours, while a nitrogen gas was circulated at a flow rate of 500 ml/minute, and maintained for 1 hour. It was cooled to room temperature, while a nitrogen gas was circulated, and 0.100 g of black solid matter was taken out from the reaction tube. The solid matter obtained was immediately placed on a sample plate of XRD and subjected to XRD analysis. FIG. 19 shows the results obtained. FIG. 19 demonstrated that the solid matter contained CaO, Fe as an electrode material, and NaCl as a component of the molten salt.

In Examples 1 to 9, constant potential electrolysis was performed. In Examples 10 to 16, constant current electrolysis was performed. The target first metal carbide was obtained by any of the electrolytic methods.

As shown in Example 16, a metal oxide as a raw material (CaO in Example 16) can be easily reproduced and recovered from the aqueous solution after hydrolysis. The metal oxide recovered can be used again as a raw material for producing a metal carbide. This constructs a recycling system and provides an environmentally friendly process.

The present disclosure further includes the following embodiments.

[1] A method for producing a metal carbide, comprising: preparing a molten salt containing an oxide of a first metal; adding carbon dioxide to the molten salt; and obtaining precipitates containing a first metal carbide by applying a voltage to the molten salt containing carbon dioxide.

[2] The method for producing a metal carbide according to [1] above, wherein the molten salt further contains a halide of a second metal.

[3] The method for producing a metal carbide according to [2] above, wherein the first metal and the second metal are the same.

[4] The method for producing a metal carbide according to [2] or [3] above, wherein halogen in the halide contains chlorine.

[5] The method for producing a metal carbide according to [2] or [3] above, wherein the halogen in the halide contains fluorine.

[6] The method for producing a metal carbide according to any one of [1] to [5] above, wherein the precipitates further contain at least one selected from the group consisting of carbon, the simple substance, halide, carbonate, oxide, hydride, and peroxide of the first metal, and the simple substance, halide, carbonate, oxide, and carbide of a metal other than the first metal contained in the molten salt.

[7] The method for producing a metal carbide according to any one of [1] to [6] above, wherein the first metal contains at least one selected from the group consisting of alkali metals and alkaline earth metals.

[8] The method for producing a metal carbide according to any one of [1] to [7] above, wherein the first metal contains at least one selected from the group consisting of lithium, sodium, potassium, and calcium.

[9] A method for producing a hydrocarbon, comprising: preparing a molten salt containing an oxide of a first metal; adding carbon dioxide to the molten salt; obtaining precipitates containing a first metal carbide by applying a voltage to the molten salt containing carbon dioxide; and obtaining a gas containing a hydrocarbon and a hydroxide of the first metal by hydrolyzing the first metal carbide.

[10] The method for producing a hydrocarbon according to [9] above, further comprising: obtaining the oxide of the first metal by dehydrating the hydroxide; and reusing the oxide obtained for preparing the molten salt.

[11] The method for producing a hydrocarbon according to [9] or [10] above, wherein the hydrocarbon is acetylene.

[12] The method for producing a hydrocarbon according to any one of [9] to [11] above, wherein the gas contains acetylene and at least one selected from the group consisting of ethylene, ethane, methane, and hydrogen.

[13] A metal carbide composition comprising: a first metal carbide as the main component; and further at least one selected from the group consisting of carbon, the simple substance, halide, carbonate, oxide, hydride, and peroxide of the first metal, and the simple substance, halide, carbonate, oxide, and carbide of a metal other than the first metal.

INDUSTRIAL APPLICABILITY

The production method of the present disclosure is useful in various fields, particularly in the environment field, since it uses carbon dioxide, which is one of the causes for global warming, as a carbon source.

The invention claimed is:

1. A method for producing a hydrocarbon, comprising: preparing a molten salt containing an oxide of a first metal; adding carbon dioxide to the molten salt;

obtaining precipitates containing a first metal carbide by applying a voltage to the molten salt containing carbon dioxide; and obtaining a gas containing a hydrocarbon and a hydroxide of the first metal by hydrolyzing the first metal carbide.

2. The method for producing a hydrocarbon according to claim 1, further comprising:

obtaining the oxide of the first metal by dehydrating the hydroxide; and reusing the oxide obtained for preparing the molten salt.

3. The method for producing a hydrocarbon according to claim 1, wherein the hydrocarbon is acetylene.

4. The method for producing a hydrocarbon according to claim 1, wherein the gas contains acetylene and at least one selected from the group consisting of ethylene, ethane, methane, and hydrogen.

\* \* \* \* \*